US010624990B2

(12) United States Patent
Malinin

(10) Patent No.: US 10,624,990 B2
(45) Date of Patent: Apr. 21, 2020

(54) BIOACTIVE IMPLANTS AND METHODS OF MAKING AND USING

(71) Applicant: Osteolife Biomedical, LLC, Miami, FL (US)

(72) Inventor: Theodore Malinin, Key Biscayne, FL (US)

(73) Assignee: Osteolife Biomedical, LLC, Miami, FL (US)

( * ) Notice: Subject to any disclaimer, the term of this patent is extended or adjusted under 35 U.S.C. 154(b) by 0 days.

(21) Appl. No.: 16/148,289

(22) Filed: Oct. 1, 2018

(65) Prior Publication Data

US 2019/0030209 A1   Jan. 31, 2019

Related U.S. Application Data

(62) Division of application No. 14/937,206, filed on Nov. 10, 2015, now abandoned.

(51) Int. Cl.
  *A61L 27/36* (2006.01)
  *A61L 27/50* (2006.01)
  *A61L 27/54* (2006.01)

(52) U.S. Cl.
  CPC ....... *A61L 27/3608* (2013.01); *A61L 27/3612* (2013.01); *A61L 27/50* (2013.01);
  (Continued)

(58) Field of Classification Search
  None
  See application file for complete search history.

(56) References Cited

U.S. PATENT DOCUMENTS 4,172,128 A   10/1979 Thiele et al.
4,191,747 A    3/1980 Scheicher
(Continued)

FOREIGN PATENT DOCUMENTS

CN   1861197   11/2006

OTHER PUBLICATIONS

Povidone-Iodine Prevents Infection in Prosthetic Implants, Outpatient Surgery, Mar. 7, 2011, accessed online at http://www.outpatientsurgery.net/newsletter/eweekly/2011/03/08/povidone-iodine-prevents-infection-in-prosthetic-implants. (Year: 2011).*
(Continued)

*Primary Examiner* — Carlos A Azpuru
*Assistant Examiner* — Casey S Hagopian
(74) *Attorney, Agent, or Firm* — Akerman LLP

(57) ABSTRACT

The present application relates to bioactive implants, methods of making bioactive implants, and methods of using bioactive implants to treat or repair a bone defect or a cartilage defect. In an aspect, the present application relates to compositions comprising bone microparticles in a solution, wherein the compositions harden upon desiccation into bioactive implants. In an aspect, the present application relates to compositions comprising cartilage microparticles in a solution, wherein the compositions harden upon desiccation into bioactive implants. In an aspect, disclosed herein are methods of making and using the disclosed compositions comprising bone microparticles and the disclosed composition comprising cartilage microparticles. This abstract is intended as a scanning tool for purposes of searching in the particular art and is not intended to be limiting of the present invention.

7 Claims, 3 Drawing Sheets

(52) U.S. Cl.
CPC ......... *A61L 27/54* (2013.01); *A61L 2300/106* (2013.01); *A61L 2300/404* (2013.01); *A61L 2430/02* (2013.01); *A61L 2430/06* (2013.01)

(56) References Cited

U.S. PATENT DOCUMENTS

| | | | |
|---|---|---|---|
| 4,277,238 | A | 7/1981 | Katagirl |
| 4,394,370 | A | 7/1983 | Jefferies |
| 4,725,234 | A | 2/1988 | Ethridge |
| 4,743,259 | A | 5/1988 | Bolander et al. |
| 4,851,046 | A | 7/1989 | Low et al. |
| 4,904,261 | A | 2/1990 | Dove |
| 4,932,973 | A | 6/1990 | Gendler |
| 5,053,049 | A | 10/1991 | Campbell |
| 5,073,373 | A | 12/1991 | O'Leary et al. |
| 5,112,354 | A | 5/1992 | Sires |
| 5,290,558 | A | 3/1994 | O'Leary et al. |
| 5,306,304 | A | 4/1994 | Gendler |
| 5,458,638 | A | 10/1995 | Kuslich |
| 5,464,439 | A | 11/1995 | Gendler |
| 5,507,813 | A | 4/1996 | Dowd |
| 5,516,532 | A | 5/1996 | Atala et al. |
| 5,556,430 | A | 9/1996 | Gendler |
| 5,756,145 | A * | 5/1998 | Darouiche .......... A61F 2/30767 427/2.24 |
| 5,860,973 | A | 1/1999 | Michelson |
| 5,866,155 | A | 2/1999 | Laurencin et al. |
| 6,030,635 | A | 2/2000 | Gertzman et al. |
| 6,224,630 | B1 | 5/2001 | Bao |
| 6,241,771 | B1 | 6/2001 | Gresser |
| 6,245,108 | B1 | 6/2001 | Biscup |
| 6,277,149 | B1 | 8/2001 | Boyle |
| 6,293,970 | B1 | 9/2001 | Wolfinbarger, Jr. et al. |
| 6,325,806 | B1 | 12/2001 | Fox |
| 6,530,955 | B2 | 3/2003 | Boyle |
| 6,576,249 | B1 | 6/2003 | Gendler et al. |
| 6,591,581 | B2 | 7/2003 | Schmieding |
| 6,632,247 | B2 | 10/2003 | Boyer, II |
| 6,660,038 | B2 | 12/2003 | Boyer, II |
| 6,843,807 | B1 | 1/2005 | Boyce et al. |
| 6,855,169 | B2 | 2/2005 | Boyer, II et al. |
| 6,887,272 | B2 | 5/2005 | Shinomiya |
| 6,942,698 | B1 | 9/2005 | Jackson |
| 6,986,788 | B2 | 1/2006 | Paul |
| 7,018,412 | B2 | 3/2006 | Ferreira |
| 7,077,866 | B2 | 7/2006 | Gresser |
| 7,115,146 | B2 | 10/2006 | Boyer |
| 7,335,381 | B2 | 2/2008 | Malinin et al. |
| 7,473,277 | B2 | 1/2009 | Boyer, II |
| 7,838,040 | B2 | 11/2010 | Malinin |
| 7,879,103 | B2 | 2/2011 | Gertzman et al. |
| 8,182,532 | B2 | 5/2012 | Anderson |
| 8,202,538 | B2 | 6/2012 | Behnam et al. |
| 8,268,008 | B2 | 9/2012 | Betz et al. |
| 8,318,212 | B2 | 11/2012 | Malinin |
| 8,337,780 | B2 | 12/2012 | Gaskins et al. |
| 8,357,384 | B2 | 1/2013 | Behnam et al. |
| 8,403,986 | B2 | 3/2013 | Michelson |
| 8,574,825 | B2 | 11/2013 | Shelby et al. |
| 8,608,801 | B2 | 12/2013 | Hung et al. |
| 8,608,803 | B2 | 12/2013 | Sybert |
| 8,709,087 | B2 | 4/2014 | Cragg |
| 8,791,071 | B1 | 7/2014 | Malinin |
| 8,888,823 | B1 | 11/2014 | Malinin |
| 8,936,816 | B1 | 1/2015 | Anderson et al. |
| 8,940,692 | B2 | 1/2015 | Malinin |
| 8,940,698 | B2 | 1/2015 | Malinin |
| 9,101,424 | B1 | 8/2015 | Malinin et al. |
| 9,611,043 | B2 | 4/2017 | Malinin et al. |
| 9,839,524 | B2 | 12/2017 | Malinin et al. |
| 2001/0008980 | A1 | 7/2001 | Gresser |
| 2001/0034553 | A1 | 10/2001 | Michelson |
| 2003/0143256 | A1 | 7/2003 | Gen |
| 2004/0068234 | A1 | 4/2004 | Martin et al. |
| 2004/0107003 | A1 | 6/2004 | Boyer, II |
| 2004/0169311 | A1 | 9/2004 | Bonutti |
| 2004/0255506 | A1 | 12/2004 | Belmont et al. |
| 2005/0008672 | A1 | 1/2005 | Winterbottom et al. |
| 2005/0196460 | A1 | 9/2005 | Malinin |
| 2005/0244457 | A1 | 11/2005 | Reddi |
| 2006/0074466 | A1 | 4/2006 | Malinin |
| 2006/0206208 | A1 | 9/2006 | Michelson |
| 2006/0279625 | A1 | 12/2006 | Malinin |
| 2007/0098756 | A1 | 5/2007 | Behnam |
| 2007/0191963 | A1 | 8/2007 | Winterbottom et al. |
| 2007/0231788 | A1 | 10/2007 | Behnam et al. |
| 2008/0091270 | A1 | 4/2008 | Miller |
| 2008/0234822 | A1 | 9/2008 | Govil |
| 2008/0279825 | A1 | 11/2008 | Malinin |
| 2009/0017095 | A1 | 1/2009 | Barnouin et al. |
| 2009/0018659 | A1 | 1/2009 | Malinin |
| 2009/0155378 | A1 | 6/2009 | Behnam et al. |
| 2009/0269388 | A1 | 10/2009 | Sunwoo et al. |
| 2009/0312842 | A1 | 12/2009 | Bursac et al. |
| 2009/0318934 | A1 | 12/2009 | Johnson et al. |
| 2010/0268833 | A1 | 10/2010 | Malinin |
| 2010/0274362 | A1 * | 10/2010 | Yayon .................... A61K 35/32 623/23.72 |
| 2010/0310623 | A1 | 12/2010 | Laurencin et al. |
| 2011/0009967 | A1 | 1/2011 | Malinin |
| 2011/0071536 | A1 | 3/2011 | Kleiner et al. |
| 2011/0104242 | A1 | 5/2011 | Malinin |
| 2011/0118850 | A1 | 5/2011 | Govil et al. |
| 2011/0208190 | A1 | 8/2011 | Kumbar et al. |
| 2011/0208305 | A1 | 8/2011 | Malinin et al. |
| 2012/0121660 | A1 | 5/2012 | Akella et al. |
| 2012/0195971 | A1 | 8/2012 | Missos et al. |
| 2012/0245703 | A1 | 9/2012 | Meredith |
| 2013/0079889 | A1 | 3/2013 | Spillman |
| 2013/0108595 | A1 | 5/2013 | Gimble et al. |
| 2013/0184835 | A1 | 7/2013 | Ferrari et al. |
| 2013/0209956 | A1 | 8/2013 | Sanders |
| 2013/0316012 | A1 | 11/2013 | Gaskins et al. |
| 2013/0338792 | A1 | 12/2013 | Schmieding et al. |
| 2014/0005793 | A1 | 1/2014 | Koford et al. |
| 2014/0065239 | A9 | 3/2014 | Behnam et al. |
| 2014/0134212 | A1 | 5/2014 | Shi et al. |
| 2014/0255506 | A1 | 9/2014 | Behnam et al. |
| 2015/0012017 | A1 | 1/2015 | Koford |
| 2015/0012107 | A1 | 1/2015 | Koford et al. |
| 2015/0140096 | A1 | 2/2015 | Malinin |
| 2015/0028243 | A1 | 9/2015 | Malinin |
| 2015/0258243 | A1 | 9/2015 | Malinin |
| 2017/0112963 | A1 | 4/2017 | Malinin |
| 2017/0128633 | A1 | 5/2017 | Malinin |
| 2017/0128634 | A1 | 5/2017 | Malinin |
| 2017/0202645 | A1 | 7/2017 | Malinin |
| 2017/0266355 | A1 | 9/2017 | Malinin |

OTHER PUBLICATIONS

Povidone Iodine Solubility, PubChem, accessed online at https://pubchem.ncbi.nlm.nih.gov/compound/Povidone-iodine#section=Solubility&fullscreen=true (Source: O'Neil, M.J. The Merck Index—An Encyclopedia of Chemicals, Drugs, and Biologicals. Cambridge, UK: Royal Society of Chemistry, 2013., p. 1425). (Year: 2013).*
Malinin, T., Acquisition and Banking of Bone Allografts, Bone Grafts & Bone Substitutes, Edited by M.B. Habal and A.H. Reddi. Philadelphia, WB Saunders Company, Aug. 17, 1992, pp. 206-225.
Malinin, T. & Temple, H. T., Musculoskeletal Tissue Transplantation and Tissue Banking, Jaypee Brothers Medical Publishers (P) Ltd., New Delhi, India, Aug. 28, 2013.
International Search Report issued in connection with PCT/US2015/036384, dated Nov. 12, 2015.
Written Opinion of the International Searching Authority issued in connection with PCT/US2015/036384, dated Nov. 12, 2015.
Osteosponge, Bacterin, www.bacterin.com.
Povidone-Iodine Prevents Infection in Prosthetic Implants, Outpatient Surgery, Mar. 7, 2011, accessed online at http://www.outpatientsurgery.net/newsletter/eweekly/2011/03/08/povidone-iodine-prevents-infection-in-prosthetic-implants.

(56) References Cited

OTHER PUBLICATIONS

Malinin et al., "Particulate Bone Allograft Incorporation in Regeneration of Osseous Defects; Importance of Particle Sizes", The Open Orthopaedics Journal, 2007, vol. 1, pp. 19-24.
International Search Report issued in PCT/US2015/014618, dated May 8, 2015.
Written Opinion of the International Search Authority issued in PCT/US2015/014618, dated May 8, 2015.
U.S. Appl. No. 15/477,778, filed Apr. 3, 2017.
U.S. Appl. No. 14/923,057, filed Oct. 26, 2015.
U.S. Appl. No. 15/611,038, filed Jun. 1, 2017.

\* cited by examiner

BIOACTIVE IMPLANTS AND METHODS OF MAKING AND USING

CROSS-REFERENCE TO RELATED APPLICATIONS

This application is a divisional application and claims the benefit of the filing date under 35 U.S.C. § 120 of U.S. patent application Ser. No. 14/937,206, filed Nov. 10, 2015, the contents of which is hereby incorporated by reference into this specification.

FIELD OF THE INVENTION

The present application relates to bioactive implants, methods of making bioactive implants, and methods of using bioactive implants to treat or repair bone or cartilage defects.

BACKGROUND OF THE INVENTION

The basic elements required for bone formation include a three-dimensional, open-porosity tissue scaffold, cells, and osteoinductive signaling molecules to stimulate cell differentiation, proliferation, and matrix formation. The biologic, physical, and biomechanical properties of the materials, compositions, and constructs are some of the major factors in determining their suitability for the use in the treatment and repair of bone and cartilage defects. For example, successful bone formation requires that these elements be combined in a well-coordinated spatial and time dependent fashion. Moreover, the relative contribution of each element may vary, e.g., according to differences in patient age, gender, health, systemic conditions, habits, anatomical location, etc.

Despite advances in the understanding in the treatment and repair of bone and cartilage defects, there is still a need for bioactive implants that are biocompatible, non-inflammatory, osteogenic, and chondrogenic, and can be replaced by a subject's natural bone and cartilage.

BRIEF SUMMARY OF THE INVENTION

Disclosed herein is a composition comprising bone microparticles in a solution, wherein the composition hardens upon desiccation into a bioactive implant.

Disclosed herein is a composition comprising bone microparticles in a solution, wherein the size of the bone microparticles is from about 20 μm to about 800 μm.

Disclosed herein is a composition comprising bone microparticles in a solution, wherein the size of the bone microparticles is from about 20 μm to about 800 μm, and wherein the composition hardens upon desiccation into a bioactive implant.

Disclosed herein is a composition comprising bone microparticles in a hydroxyethyl starch solution, wherein the size of the bone microparticles is from about 20 μm to about 800 μm.

Disclosed herein is a composition comprising bone microparticles in a polyvinyl pyrrolidone (PVP) solution, wherein the size of the bone microparticles is from about 20 μm to about 800 μm.

Disclosed herein is a composition comprising bone microparticle in a povidone iodine solution, wherein the size of the bone microparticles is from about 20 μm to about 800 μm.

Disclosed herein is a composition comprising bone microparticles in a collagen solution, wherein the size of the bone microparticles is from about 20 μm to about 800 μm.

Disclosed herein is a composition comprising bone microparticles in an albumin solution, wherein the size of the bone microparticles is from about 20 μm to about 800 μm.

Disclosed herein is a composition comprising bone microparticles in a hydroxyethyl starch solution, wherein the size of the bone microparticles is from about 20 μm to about 800 μm, wherein the composition hardens upon desiccation into a bioactive implant.

Disclosed herein is a composition comprising bone microparticles in a polyvinyl pyrrolidone (PVP) solution, wherein the size of the bone microparticles is from about 20 μm to about 800 μm, and wherein the composition hardens upon desiccation into a bioactive implant.

Disclosed herein is a composition comprising bone microparticles in a povidone iodine solution, wherein the size of the bone microparticles is from about 20 μm to about 800 μm, and wherein the composition hardens upon desiccation into a bioactive implant.

Disclosed herein is a composition comprising bone microparticles in a collagen solution, wherein the size of the bone microparticles is from about 20 μm to about 800 μm, and wherein the composition hardens upon desiccation into a bioactive implant.

Disclosed herein is a composition comprising bone microparticles in an albumin solution, wherein the size of the bone microparticles is from about 20 μm to about 800 μm, and wherein the composition hardens upon desiccation into a bioactive implant.

Disclosed herein is a container comprising a composition disclosed herein.

Disclosed herein is a container comprising a composition, wherein the composition comprises bone microparticles in a solution.

Disclosed herein is a container comprising a composition, wherein the composition comprises bone microparticles in a solution, wherein the size of the bone microparticles is from about 20 μm to about 800 μm.

Disclosed herein is a container comprising a composition comprising bone microparticles in a hydroxyethyl starch solution, wherein the size of the bone microparticles is from about 20 μm to about 800 μm, and wherein the composition hardens upon desiccation into a bioactive implant.

Disclosed herein is a container comprising a composition comprising bone microparticles in a polyvinyl pyrrolidone (PVP) solution, wherein the size of the bone microparticles is from about 20 μm to about 800 μm, and wherein the composition hardens upon desiccation into a bioactive implant.

Disclosed herein is a container comprising a composition comprising bone microparticles in a povidone iodine solution, wherein the size of the bone microparticles is from about 20 μm to about 800 μm, and wherein the composition hardens upon desiccation into a bioactive implant.

Disclosed herein is container comprising a composition comprising bone microparticles in a collagen solution, wherein the size of the bone microparticles is from about 20 μm to about 800 μm, and wherein the composition hardens upon desiccation into a bioactive implant.

Disclosed herein is a container comprising a composition comprising bone microparticles in an albumin solution, wherein the size of the bone microparticles is from about 20 μm to about 800 μm, and wherein the composition hardens upon desiccation into a bioactive implant.

Disclosed herein is a kit comprising a container disclosed herein.

Disclosed herein is a kit comprising a container disclosed herein, wherein the container comprises a composition disclosed herein.

Disclosed herein is a kit comprising a container, wherein the container comprises a composition comprising bone microparticles in a solution.

Disclosed herein is a kit comprising a container, wherein the container comprises a composition comprising bone microparticles in a solution, wherein the size of the bone microparticles is from about 20 µm to about 800 µm.

Disclosed herein is a kit comprising (i) bone microparticles, and (ii) instructions for preparing a composition comprising bone microparticles in a solution.

Disclosed herein is a kit comprising (i) bone microparticles, (ii) hydroxyethyl starch, and (iii) instructions for preparing a composition comprising bone microparticles in a hydroxyethyl starch solution.

Disclosed herein is a kit comprising (i) bone microparticles, (ii) hydroxyethyl starch, (iii) at least one mold of a pre-determined size and shape, (iv) instructions for preparing a composition comprising bone microparticles in a hydroxyethyl starch solution, and (v) instructions for using the composition.

Disclosed herein is a kit comprising (i) bone microparticles, (ii) at least one mold of a pre-determined size and shape, (iii) instructions for preparing a composition comprising bone microparticles in a hydroxyethyl starch solution, and (iv) instructions for using the composition.

Disclosed herein is a bioactive implant made by a method comprising desiccating a composition disclosed herein.

Disclosed herein is a bioactive implant made by a method comprising desiccating a composition comprising bone microparticles in a solution.

Disclosed herein is a bioactive implant made by a method comprising desiccating a composition comprising bone microparticles in a solution, wherein the size of the bone microparticles is from about 20 µm to about 800 µm.

Disclosed herein is a bioactive implant made by a method comprising desiccating a composition comprising bone microparticles in a hydroxyethyl starch solution, wherein the size of the bone microparticles is from about 20 µm to about 800 µm.

Disclosed herein is a bioactive implant made by a method comprising adding to a mold a disclosed composition and desiccating the composition.

Disclosed herein is a bioactive implant made by a method comprising adding to a mold a composition comprising bone microparticles in a solution and desiccating the composition.

Disclosed herein is a bioactive implant made by a method comprising preparing a composition comprising bone microparticles in a solution; adding to a mold the composition; and desiccating the composition.

Disclosed herein is a bioactive implant made by a method comprising adding to a mold a composition comprising bone microparticles in a solution, wherein the size of the bone microparticles is from about 20 µm to about 800 µm; and desiccating the composition.

Disclosed herein is a bioactive implant made by a method comprising preparing a composition comprising bone microparticles in a solution, wherein the size of the bone microparticles is from about 20 µm to about 800 µm; adding to a mold the composition; and desiccating the composition.

Disclosed herein is a bioactive implant made by a method comprising desiccating a composition comprising bone microparticles in a polyvinyl pyrrolidone (PVP) solution, wherein the size of the bone microparticles is from about 20 µm to about 800 µm.

Disclosed herein is a bioactive implant made by a method comprising desiccating a composition comprising bone microparticles in a povidone iodine solution, wherein the size of the bone microparticles is from about 20 µm to about 800 µm.

Disclosed herein is a bioactive implant made by a method comprising desiccating a composition comprising bone microparticles in a collagen solution, wherein the size of the bone microparticles is from about 20 µm to about 800 µm.

Disclosed herein is a bioactive implant made by a method comprising desiccating a composition comprising bone microparticles in an albumin solution, wherein the size of the bone microparticles is from about 20 µm to about 800 µm.

Disclosed herein is a method of making a bioactive implant, the method comprising desiccating a composition disclosed herein.

Disclosed herein is a method of making a bioactive implant, the method comprising desiccating a composition comprising bone microparticles in a solution.

Disclosed herein is a method of making a bioactive implant, the method comprising desiccating a composition comprising bone microparticles in a solution, wherein the size of the bone microparticles is from about 20 µm to about 800 µm.

Disclosed herein is a method of making a bioactive implant, the method comprising adding to a mold a disclosed composition; and desiccating the composition.

Disclosed herein is a method of making a bioactive implant, the method comprising adding to a mold a composition comprising bone microparticles in a solution; and desiccating the composition.

Disclosed herein is a method of making a bioactive implant, the method comprising preparing a composition comprising bone microparticles in a solution; adding to a mold the composition; and desiccating the composition.

Disclosed herein is a method of making a bioactive implant, the method comprising adding to a mold a composition comprising bone microparticles in a solution, wherein the size of the bone microparticles is from about 20 µm to about 800 µm; and desiccating the composition.

Disclosed herein is a method of making a bioactive implant, the method comprising preparing a composition comprising bone microparticles in a solution, wherein the size of the bone microparticles is from about 20 µm to about 800 µm; adding to a mold the composition; and desiccating the composition.

Disclosed herein is a method of making a bioactive implant, the method comprising desiccating a composition comprising bone microparticles in a hydroxyethyl starch solution, wherein the size of the bone microparticles is from about 20 µm to about 800 µm.

Disclosed herein is a method of making a bioactive implant, the method comprising desiccating a composition comprising bone microparticles in a polyvinyl pyrrolidone (PVP) solution, wherein the size of the bone microparticles is from about 20 µm to about 800 µm.

Disclosed herein is a method of making a bioactive implant, the method comprising desiccating a composition comprising bone microparticles in a povidone iodine solution, wherein the size of the bone microparticles is from about 20 µm to about 800 µm.

Disclosed herein is a method of making a bioactive implant, the method comprising desiccating a composition comprising bone microparticles in a collagen solution, wherein the size of the bone microparticles is from about 20 µm to about 800 µm.

Disclosed herein is a method of making a bioactive implant, the method comprising desiccating a composition comprising bone microparticles in an albumin solution, wherein the size of the bone microparticles is from about 20 µm to about 800 µm.

Disclosed herein is a method of treating or repairing a bone defect, the method comprising generating a bioactive implant; and implanting the bioactive implant at the site of a bone defect.

Disclosed herein is a method of making a bioactive implant with one or more smooth and even surfaces, the method comprising desiccating a composition disclosed herein.

Disclosed herein is a method of making a bioactive implant with one or more rough and uneven surfaces, the method comprising desiccating a composition disclosed herein.

Disclosed herein is a method of making a bioactive implant with one or more smooth and even surfaces, the method comprising desiccating a composition comprising bone microparticles in a solution, wherein the size of the bone microparticles is from about 20 µm to about 800 µm.

Disclosed herein is a method of making a bioactive implant with one or more rough and uneven surfaces, the method comprising desiccating a composition comprising bone microparticles in a solution, wherein the size of the bone microparticles is from about 20 µm to about 800 µm.

Disclosed herein is a method of treating or repairing a bone defect, the method comprising implanting at the site of a bone a bioactive implant made by a method disclosed herein.

Disclosed herein is a method of treating or repairing a bone defect, the method comprising: preparing a composition comprising bone microparticles in a solution, wherein the size of the bone microparticles is from about 20 µm to about 800 µm; adding the composition to a mold; desiccating the composition, thereby producing the bioactive implant; and implanting the bioactive implant at the site of a bone defect.

Disclosed herein is a method of treating or repairing a bone defect, the method comprising: preparing a composition comprising bone microparticles in a hydroxyethyl starch solution, wherein the size of the bone microparticles is from about 20 µm to about 800 µm; adding the composition to a mold; desiccating the composition, thereby producing the bioactive implant; and implanting the bioactive implant at the site of a bone defect.

Disclosed herein is a composition comprising cartilage microparticles in a solution, wherein the composition hardens upon desiccation into a bioactive implant.

Disclosed herein is a composition comprising cartilage microparticles in a solution, wherein the size of the cartilage microparticles is from about 50 µm to about 900 µm.

Disclosed herein is a composition comprising cartilage microparticles in a solution, wherein the size of the cartilage microparticles is from about 50 µm to about 900 µm, and wherein the composition hardens upon desiccation into a bioactive implant.

Disclosed herein is a composition comprising cartilage microparticles in a hydroxyethyl starch solution, wherein the size of the cartilage microparticles is from about 50 µm to about 900 µm.

Disclosed herein is a composition comprising cartilage microparticles in a polyvinyl pyrrolidone (PVP) solution, wherein the size of the cartilage microparticles is from about 50 µm to about 900 µm.

Disclosed herein is a composition comprising cartilage microparticles in a povidone iodine solution, wherein the size of the cartilage microparticles is from about 50 µm to about 900 µm.

Disclosed herein is a composition comprising cartilage microparticles in a collagen solution, wherein the size of the cartilage microparticles is from about 50 µm to about 900 µm.

Disclosed herein is a composition comprising cartilage microparticles in an albumin solution, wherein the size of the cartilage microparticles is from about 50 µm to about 900 µm.

Disclosed herein is a composition comprising cartilage microparticles in a hydroxyethyl starch solution, wherein the size of the cartilage microparticles is from about 50 µm to about 900 µm, wherein the composition hardens upon desiccation into a bioactive implant.

Disclosed herein is a composition comprising cartilage microparticles in a polyvinyl pyrrolidone (PVP) solution, wherein the size of the cartilage microparticles is from about 50 µm to about 900 µm, and wherein the composition hardens upon desiccation into a bioactive implant.

Disclosed herein is a composition comprising cartilage microparticles in a povidone iodine solution, wherein the size of the cartilage microparticles is from about 50 µm to about 900 µm, and wherein the composition hardens upon desiccation into a bioactive implant.

Disclosed herein is a composition comprising cartilage microparticles in a collagen solution, wherein the size of the cartilage microparticles is from about 50 µm to about 900 µm, and wherein the composition hardens upon desiccation into a bioactive implant.

Disclosed herein is a composition comprising cartilage microparticles in an albumin solution, wherein the size of the cartilage microparticles is from about 50 µm to about 900 µm, and wherein the composition hardens upon desiccation into a bioactive implant.

Disclosed herein is a container comprising a composition, wherein the composition comprises cartilage microparticles in a solution.

Disclosed herein is a container comprising a composition, wherein the composition comprises cartilage microparticles in a solution, wherein the size of the cartilage microparticles is from about 50 µm to about 900 µm.

Disclosed herein is a container comprising a composition cartilage microparticles in a hydroxyethyl starch solution, wherein the size of the cartilage microparticles is from about 50 µm to about 900 µm, and wherein the composition hardens upon desiccation into a bioactive implant.

Disclosed herein is a container comprising a composition comprising cartilage microparticles in a polyvinyl pyrrolidone (PVP) solution, wherein the size of the cartilage microparticles is from about 50 µm to about 900 µm, and wherein the composition hardens upon desiccation into a bioactive implant.

Disclosed herein is a container comprising a composition comprising cartilage microparticles in a povidone iodine solution, wherein the size of the cartilage microparticles is from about 50 µm to about 900 µm, and wherein the composition hardens upon desiccation into a bioactive implant.

Disclosed herein is container comprising a composition comprising cartilage microparticles in a collagen solution, wherein the size of the cartilage microparticles is from about 50 μm to about 900 μm, and wherein the composition hardens upon desiccation into a bioactive implant.

Disclosed herein is a container comprising a composition cartilage microparticles in an albumin solution, wherein the size of the cartilage microparticles is from about 50 μm to about 900 μm, and wherein the composition hardens upon desiccation into a bioactive implant.

Disclosed herein is a kit comprising a container, wherein the container comprises a composition comprising cartilage microparticles in a solution.

Disclosed herein is a kit comprising a container, wherein the container comprises a composition comprising cartilage microparticles in a solution, wherein the size of the cartilage microparticles is from about 50 μm to about 900 μm.

Disclosed herein is a kit comprising (i) cartilage microparticles, and (ii) instructions for preparing a composition comprising cartilage microparticles in a solution.

Disclosed herein is a kit comprising (i) cartilage microparticles, (ii) hydroxyethyl starch, and (iii) instructions for preparing a composition comprising cartilage microparticles in a hydroxyethyl starch solution.

Disclosed herein is a kit comprising (i) cartilage microparticles, (ii) hydroxyethyl starch, (iii) at least one mold of a pre-determined size and shape, (iv) instructions for preparing a composition comprising cartilage microparticles in a hydroxyethyl starch solution, and (v) instructions for using the composition.

Disclosed herein is a kit comprising (i) cartilage microparticles, (ii) at least one mold of a pre-determined size and shape, (iii) instructions for preparing a composition comprising cartilage microparticles in a hydroxyethyl starch solution, and (iv) instructions for using the composition.

Disclosed herein is a bioactive implant made by a method comprising desiccating a composition comprising cartilage microparticles in a solution.

Disclosed herein is a bioactive implant made by a method comprising desiccating a composition comprising cartilage microparticles in a solution, wherein the size of the cartilage microparticles is from about 50 μm to about 900 μm.

Disclosed herein is a bioactive implant made by a method comprising desiccating a composition comprising cartilage microparticles in a hydroxyethyl starch solution, wherein the size of the cartilage microparticles is from about 50 μm to about 900 μm.

Disclosed herein is a bioactive implant made by a method comprising adding to a mold a disclosed composition and desiccating the composition.

Disclosed herein is a bioactive implant made by a method comprising adding to a mold a composition comprising cartilage microparticles in a solution and desiccating the composition.

Disclosed herein is a bioactive implant made by a method comprising preparing a composition comprising cartilage microparticles in a solution; adding to a mold the composition; and desiccating the composition.

Disclosed herein is a bioactive implant made by a method comprising adding to a mold a composition comprising cartilage microparticles in a solution, wherein the size of the cartilage microparticles is from about 50 μm to about 900 μm; and desiccating the composition.

Disclosed herein is a bioactive implant made by a method comprising preparing a composition comprising cartilage microparticles in a solution, wherein the size of the cartilage microparticles is from about 50 μm to about 900 μm; adding to a mold the composition; and desiccating the composition.

Disclosed herein is a bioactive implant made by a method comprising desiccating a composition comprising cartilage microparticles in a polyvinyl pyrrolidone (PVP) solution, wherein the size of the cartilage microparticles is from about 50 μm to about 900 μm.

Disclosed herein is a bioactive implant made by a method comprising desiccating a composition comprising cartilage microparticles in a povidone iodine solution, wherein the size of the cartilage microparticles is from about 50 μm to about 900 μm.

Disclosed herein is a bioactive implant made by a method comprising desiccating a composition comprising cartilage microparticles in a collagen solution, wherein the size of the cartilage microparticles is from about 50 μm to about 900 μm.

Disclosed herein is a bioactive implant made by a method comprising desiccating a composition comprising cartilage microparticles in an albumin solution, wherein the size of the cartilage microparticles is from about 50 μm to about 900 μm.

Disclosed herein is a method of making a bioactive implant, the method comprising desiccating a composition comprising cartilage microparticles in a solution.

Disclosed herein is a method of making a bioactive implant, the method comprising desiccating a composition comprising cartilage microparticles in a solution, wherein the size of the cartilage microparticles is from about 50 μm to about 900 μm.

Disclosed herein is a method of making a bioactive implant, the method comprising adding to a mold a composition comprising cartilage microparticles in a solution; and desiccating the composition.

Disclosed herein is a method of making a bioactive implant, the method comprising preparing a composition comprising cartilage microparticles in a solution; adding to a mold the composition; and desiccating the composition.

Disclosed herein is a method of making a bioactive implant, the method comprising adding to a mold a composition comprising cartilage microparticles in a solution, wherein the size of the cartilage microparticles is from about 50 μm to about 900 μm; and desiccating the composition.

Disclosed herein is a method of making a bioactive implant, the method comprising preparing a composition comprising cartilage microparticles in a solution, wherein the size of the cartilage microparticles is from about 50 μm to about 900 μm; adding to a mold the composition; and desiccating the composition.

Disclosed herein is a method of making a bioactive implant, the method comprising desiccating a composition comprising cartilage microparticles in a hydroxyethyl starch solution, wherein the size of the cartilage microparticles is from about 50 μm to about 900 μm.

Disclosed herein is a method of making a bioactive implant, the method comprising desiccating a composition comprising cartilage microparticles in a polyvinyl pyrrolidone (PVP) solution, wherein the size of the cartilage microparticles is from about 50 μm to about 900 μm.

Disclosed herein is a method of making a bioactive implant, the method comprising desiccating a composition comprising cartilage microparticles in a povidone iodine solution, wherein the size of the cartilage microparticles is from about 50 μm to about 900 μm.

Disclosed herein is a method of making a bioactive implant, the method comprising desiccating a composition comprising cartilage microparticles in a collagen solution, wherein the size of the cartilage microparticles is from about 50 μm to about 900 μm.

Disclosed herein is a method of making a bioactive implant, the method comprising desiccating a composition comprising cartilage microparticles in an albumin solution, wherein the size of the cartilage microparticles is from about 50 µm to about 900 µm.

Disclosed herein is a method of treating or repairing a cartilage defect, the method comprising generating a bioactive implant; and implanting the bioactive implant at the site of a cartilage defect.

Disclosed herein is a method of making a bioactive implant with one or more smooth and even surfaces, the method comprising desiccating a composition comprising cartilage microparticles in a solution, wherein the size of the cartilage microparticles is from about 50 µm to about 900 µm.

Disclosed herein is a method of making a bioactive implant with one or more rough and uneven surfaces, the method comprising desiccating a composition comprising cartilage microparticles in a solution, wherein the size of the cartilage microparticles is from about 50 µm to about 900 µm.

Disclosed herein is a method of treating or repairing a cartilage defect, the method comprising implanting at the site of a cartilage defect a bioactive implant made by a method disclosed herein.

Disclosed herein is a method of treating or repairing a cartilage defect, the method comprising: preparing a composition comprising cartilage microparticles in a solution, wherein the size of the cartilage microparticles is from about 50 µm to about 900 µm; adding the composition to a mold; desiccating the composition, thereby producing the bioactive implant; and implanting the bioactive implant at the site of a cartilage defect.

Disclosed herein is a method of treating or repairing a cartilage defect, the method comprising: preparing a composition comprising cartilage microparticles in a hydroxyethyl starch solution, wherein the size of the cartilage microparticles is from about 50 µm to about 900 µm; adding the composition to a mold; desiccating the composition, thereby producing the bioactive implant; and implanting the bioactive implant at the site of a cartilage defect.

Figure 1A:
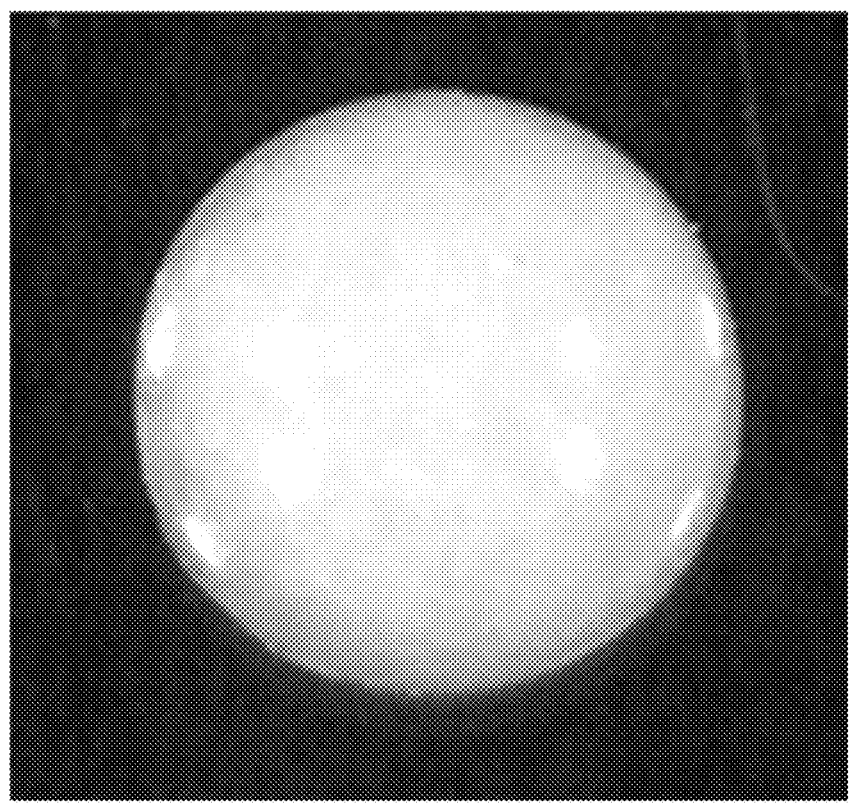
FIG. 1A shows a bioactive implant made by desiccating in a vacuum a composition comprising bone microparticles (25% w/v) in a 6% HES solution. The surface of the bioactive implant was smooth and glistening.
Figure 1B:
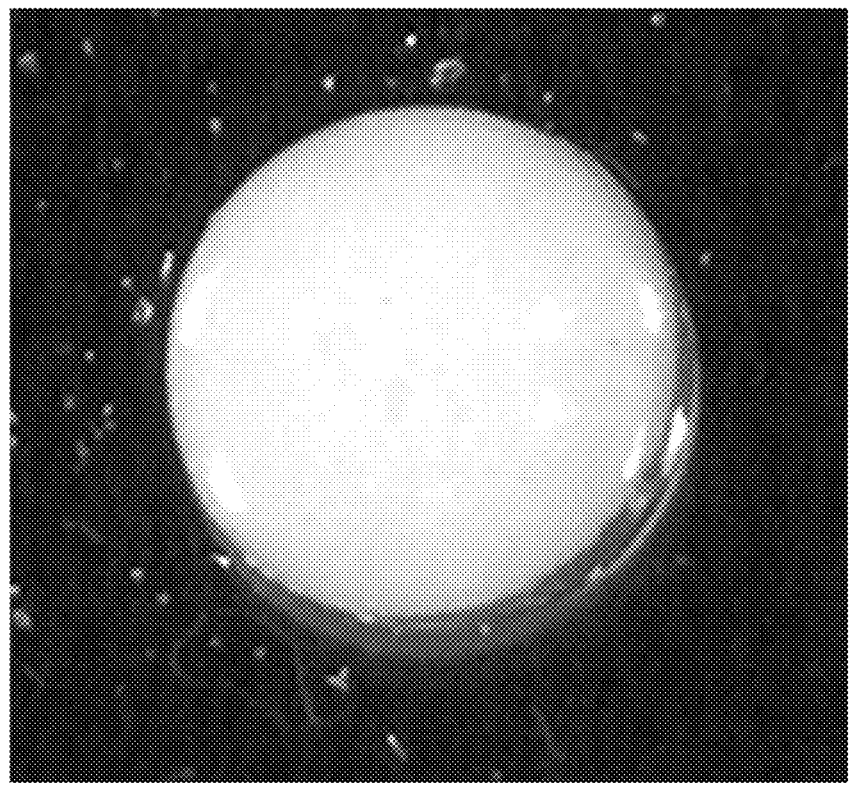
FIG. 1B shows a bioactive implant made by desiccating in a vacuum a composition comprising bone microparticles (25% w/v) in a 25% w/v PVP solution (MW=40,000).
Figure 1C:
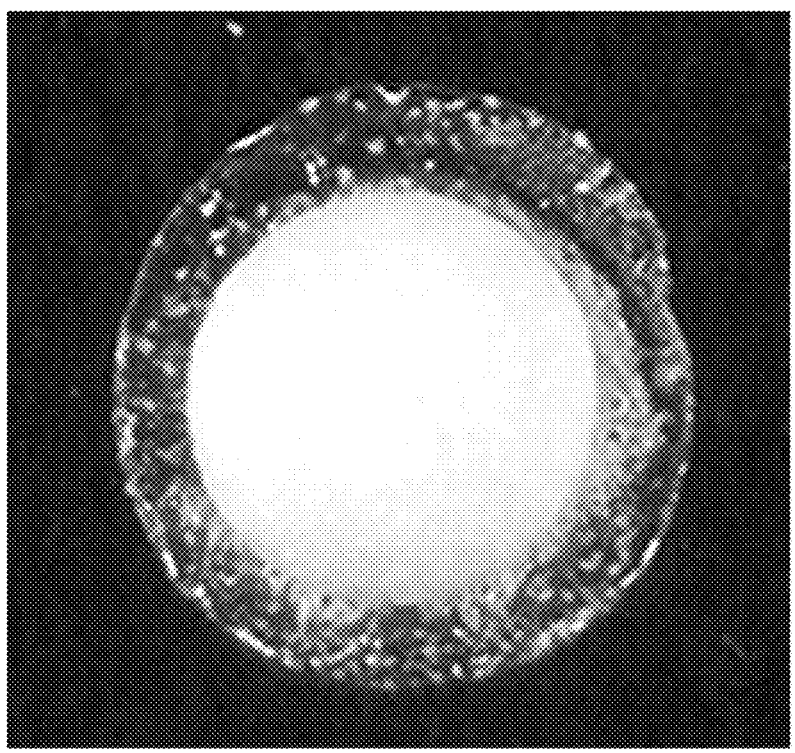
FIG. 1C shows a bioactive implant made by desiccating in a vacuum a composition comprising bone microparticles in a human bone collage solution. Bone microparticles particles were visible in a thin layer of collagen, which escaped the mold.
Figure 1D:
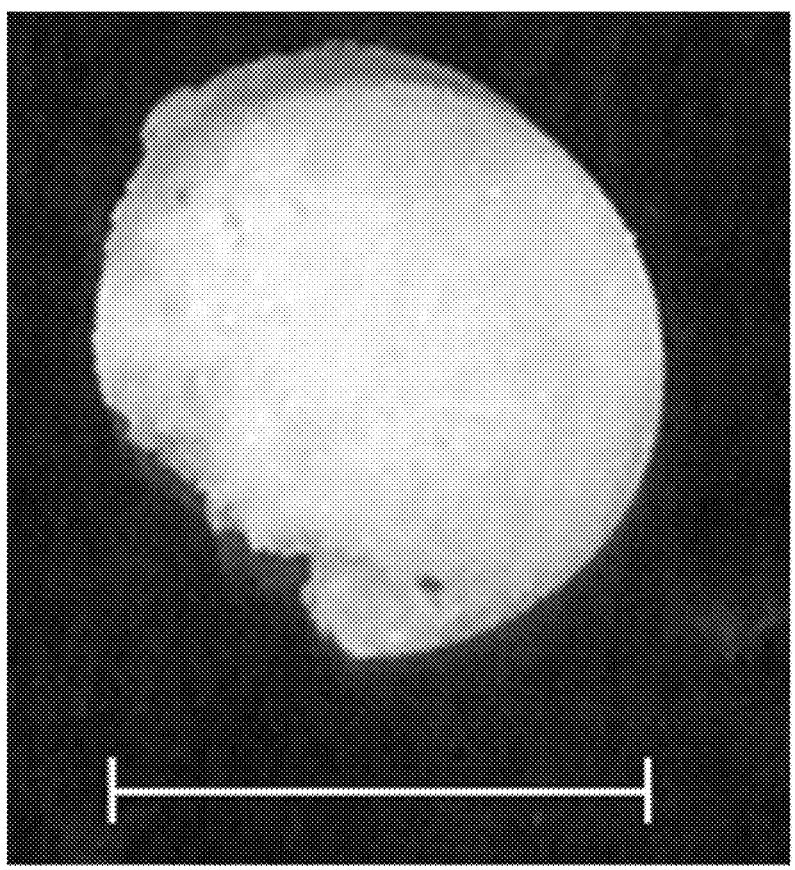
FIG. 1D shows a bioactive implant made by desiccating in a vacuum a composition comprising bone microparticles in an albumin solution. The surface of the bioactive implant was rough and uneven and the texture was brittle. The bar at the bottom of photograph is 1.5 cm long.
Figure 2A:
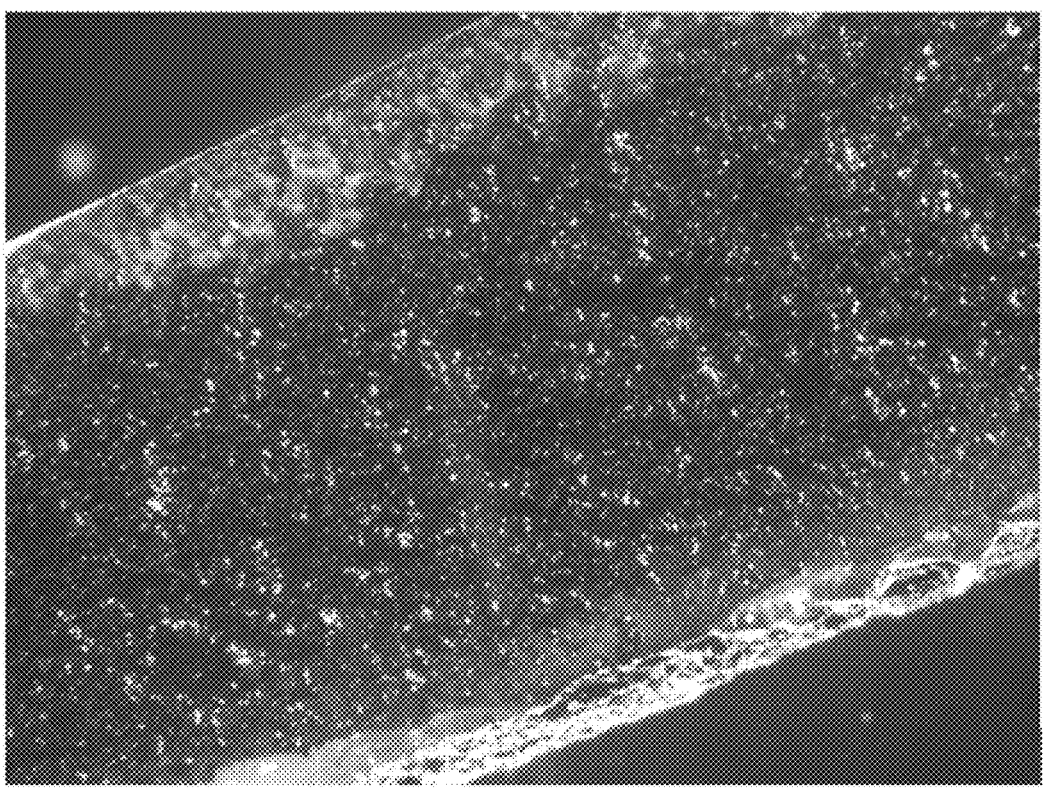
FIG. 2A shows a section of bone microparticles embedded in an HES solution, when viewed in polarized light under 10% magnification. Evenly distributed bone particles were doubly refractile.
Figure 2B:
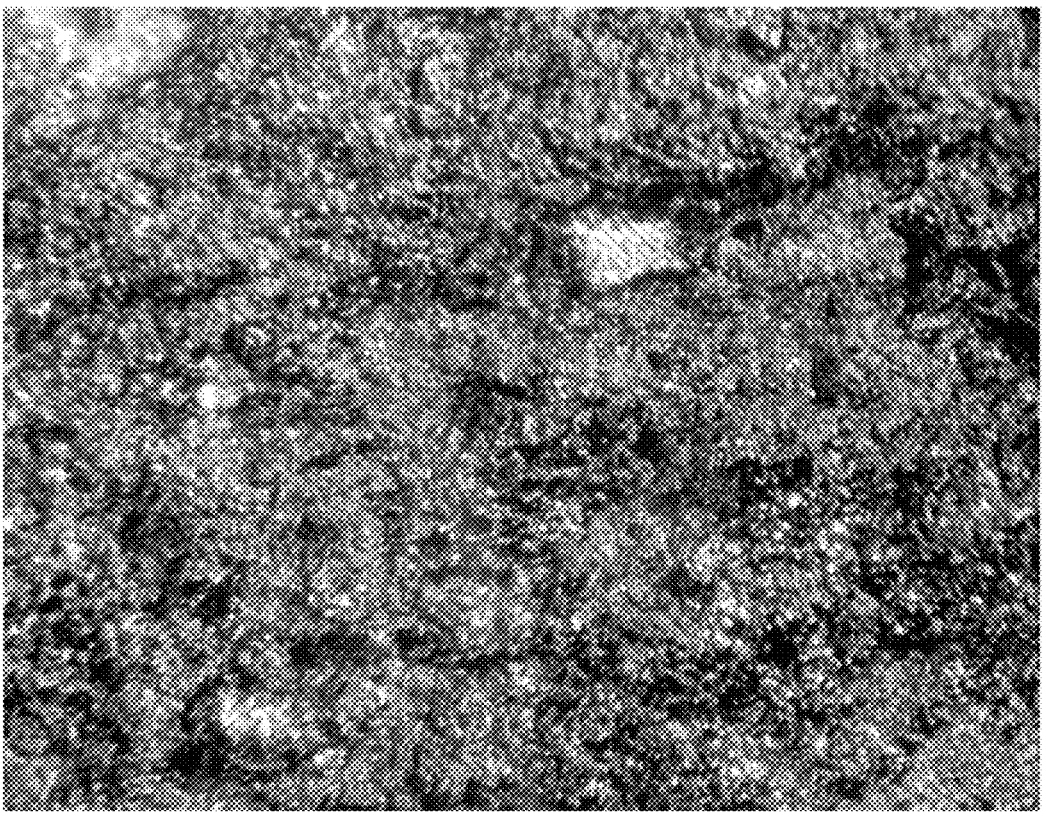
FIG. 2B shows a 25× magnification of the image shown in FIG. 2A. Evenly spaced doubly refractile bone particles were clearly visible.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. Definitions

As used in the specification and the appended claims, the singular forms "a", "an", and "the" include plural referents unless the context clearly dictates otherwise.

The phrase "consisting essentially of" limits the scope of a claim to the recited components in a composition or the recited steps in a method as well as those that do not materially affect the basic and novel characteristic or characteristics of the claimed composition or claimed method.

The phrase "consisting of" excludes any component, step, or element that is not recited in the claim.

The phrase "comprising" is synonymous with "including", "containing", or "characterized by", and is inclusive or open-ended. "Comprising" does not exclude additional, unrecited components or steps.

As used herein when referring to any numerical value, the term "about" means a value falling within a range that is ±10% of the stated value.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. For example, in an aspect, a disclosed method can optionally comprise one or more additional steps, such as, for example, repeating an administering step or altering an administering step.

As known to the art, a solution is a homogeneous mixture of two or more substances. A solution may exist in any phase. For example, a solution can be a homogeneous mixture composed of only one phase, wherein a solute (such as, e.g., HES, non-solubilized HES, polyvinyl pyrrolidone (PVP), povidone iodine, bone collagen, tendon collagen, albumin, or a combination thereof) is dissolved in a solvent (such as, e.g., water, saline, alcohol, DMSO, or a combination thereof). In an aspect, solution disclosed herein is non-toxic. In an aspect, a disclosed solution comprises non-toxic components. In an aspect, a disclosed solution is safe for administration to human beings or other mammals.

As used herein, the term "subject" refers to the target of administration or implantation, e.g., an animal. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject can be a vertebrate, such as a mammal, a fish, a bird, a reptile, or an amphibian. Alternatively, the subject can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In an aspect, a subject can be human. For example, a subject can have a bone or cartilage defect, or a subject can have multiple bone or cartilage defects.

A "patient" refers to a subject afflicted with one or more diseases or disorders or conditions, such as, for example, one or more bone or cartilage defects. In an aspect, a bone or cartilage can require medical intervention. A patient can refer to a subject that has been diagnosed with or is suspected of having a bone or cartilage defect.

As used herein, the term "treatment" refers to the medical management of a patient with the intent to cure, ameliorate, stabilize, or prevent a disease, pathological condition, or disorder (such as, for example, a bone or cartilage defect). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

In an aspect, "treating" means improving or eliminating a bone or cartilage defect. In an aspect, "treating" means reducing the effects of a bone or cartilage defect or the symptoms of a bone or cartilage defect. Thus, in an aspect of a disclosed method, treating can refer to a 10%, 20%, 30%, 40%, 50%, 60%, 70%, 80%, 90%, or 100% reduction in the severity of an established bone or cartilage defect or symptoms of a bone or cartilage defect. For example, a method for treating a bone or cartilage defect can reduce one or more symptoms of a bone or cartilage defect in a subject by 10% as compared to a control. In an aspect, a reduction of one or more symptoms can be 20%, 30%, 40%, 50%, 60%, 70%, 80%, 90%, 100%, or any percent reduction in between 10% and 100% as compared to a control. It is understood that treatment does not necessarily refer to a cure or complete ablation or eradication of the bone or cartilage defect. However, in an aspect, treatment can refer to a cure or complete ablation or eradication of the bone or cartilage defect.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. In an aspect, preventing the worsening of a bone or cartilage defect or the severity of a bone or cartilage defect is intended.

As used herein, the term "diagnosed" means having been subjected to a physical examination by a person of skill, for example, a physician, and found to have a condition that can be diagnosed or treated by the composition, bioactive implants, and methods disclosed herein. For example, "diagnosed with a bone or cartilage defect" means having been subjected to a physical examination by a person of skill, for example, a physician, and found to have a condition that can be diagnosed or can be treated by a composition or bioactive implant disclosed herein, such as, for example, a bioactive implant that can treat or prevent the worsening of severity of a bone or cartilage defect. For example, "suspected of having a bone or cartilage defect" can mean having been subjected to a physical examination by a person of skill, for example, a physician, and found to have a condition that can be likely be diagnosed as or can likely be treated by a composition or bioactive implant that can treat or repair a bone or cartilage defect.

As used herein, the terms "administering" and "administration" refer to any method of providing a disclosed agent or a pharmaceutical preparation comprising a disclosed agent to a subject. Such methods are well known to those skilled in the art and include, but are not limited to: oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In an aspect, the skilled person can determine an efficacious dose, an efficacious schedule, and an efficacious route of administration for a disclosed composition or a disclosed complex so as to treat a subject or inhibit or prevent an inflammatory reaction. In an aspect, the skilled person can also alter, change, or modify an aspect of an administering step so as to improve efficacy of a disclosed agent or a pharmaceutical preparation comprising a disclosed agent.

As used herein, "modifying the method" can comprise modifying or changing one or more features or aspects of one or more steps of a disclosed method. For example, in an aspect, a method can be altered by changing the dose or the amount of a disclosed agent or a pharmaceutical preparation comprising a disclosed agent, or by changing the duration or frequency of the administration of a disclosed agent or pharmaceutical preparation comprising a disclosed agent.

As used herein, "growth factors" can refer to proteins that bind to receptors on the cell surface, with the primary result of activating cellular proliferation and/or differentiation. Many growth factors are quite versatile, stimulating cellular division in numerous different cell types; while others are specific to a particular cell-type. The art is familiar with growth factors, which include, but are not limited to, fibroblast growth factor-2 (FGF-2), insulin-like growth factor-I and -II (IGF-I and IGF-II), platelet derived growth factor (PDGF), and transforming growth factor-beta 1 (TGF-β).

As used herein, "bone" can refer to two bone tissue categories. Cortical bone represents one category while cancellous bone, which is spongy interior bone tissue, represents the second category. Cortical bone has a much higher density than cancellous bone, but it is less porous (about 5-10% for cortical bone vs. about 50-90% for cancellous bone). This means compact bone has fewer spaces and cavities than spongy bone. Despite these differences, compact and spongy bone tissue work together as cortical tissue is the shell that covers the cancellous bone of the vertebrae and joint ends In an aspect, the disclosed cartilage microparticles can be prepared as follows. Articular cartilage can be obtained from the articular surfaces of joints, such as from distal femurs, proximal tibias, acetabulums, heads of femurs, and/or heads of radiuses. The cartilage can be removed, for example, with a scalpel blade and can be removed down to subchondral bone, without removing bone. The articular cartilage can include articular hyaline cartilage and/or fibrocartilage. In an aspect, the cartilage is not subjected to harsh chemical treatments, which can alter the inherent natural properties of material within the cartilage. For example, the cartilage is not subjected to demineralization treatments such as treatment with hydrochloric acid, ethylene diamine, and/or other demineralization agents. In an aspect, the non-demineralized articular cartilage can be subjected to microbiological testing or can be subjected to other testing protocols that do not deleteriously alter the cartilage. In an aspect, the articular cartilage is not subjected to any physical treatments that may demineralize and/or alter the inherent natural properties of the cartilage. For example, the articular cartilage is not subjected to elevated temperatures, e.g., temperatures greater than about 50° C., as elevated temperatures can diminish the chondrogenic activity of the cartilage. However, the articular cartilage can be preserved, e.g., freeze-dried, frozen, and/or dried, after being removed from the joint. In an aspect, a preferred method of preserving articular cartilage can be freeze-drying.

In an aspect, the disclosed cartilage microparticles can be produced by grinding the cartilage. Prior to grinding, the cartilage can be dry cartilage, freeze-dried cartilage, frozen cartilage, wet cartilage, or a combination thereof. Pieces of cartilage obtained from the articular surface of one or more joints can be washed in several changes of normal saline, blotted dry, and frozen rapidly, e.g., at 10° C./min or faster, in the vapor phase of liquid nitrogen (about −150° C.), or alternatively, frozen rapidly in the liquid phase of liquid nitrogen (about −196° C.). After being frozen, the cartilage can be rapidly placed directly on the shelves of a freeze-drying apparatus maintained at about −40° C. to about −50° C. (the condenser being cooled to from about −70° C. to about −80° C.). In an aspect, a vacuum level of less than about 100 millitorr can be maintained in the freeze-drying chamber during the freeze-drying cycle. In an aspect, a vacuum level of about 100 millitorr to about 400 millitorr can be maintained in the freeze-drying chamber during the freeze-drying cycle. In an aspect, the freeze-drying cycle can last an average of about 5 days. In an aspect, during the initial 30-45 minutes of the cycle, the cartilage can warm from the initial frozen temperature (e.g., about −150° C.) to the temperature of the freeze-drying chamber (e.g., about −40° C.), after which it can be maintained at about −40° C. for the remainder of the cycle. In an aspect, the moisture content of the cartilage can be reduced to from about 4 to about 5%. Overdrying should be avoided, as this can result in the irreversible alterations of collagen and proteoglycan structures. In an aspect, at the end of the freeze-drying cycle, the chamber can be warmed to room temperature, the vacuum can be released, and the freeze-dried cartilage can be removed. The cartilage can be ground using any suitable grinding apparatus. For example, any grinding apparatus capable of grinding dry, hard, brittle material in seconds, such as turbo mills, disc mills, toothed disc mills, jet mills, or other similar apparatuses can be used.

In an aspect, grinding can be performed under conditions that preclude raising the temperature of the cartilage to a level that can diminish the chondrogenic activity of the resulting composition. For example, in an aspect, grinding can be performed without raising the temperature of the articular cartilage above about 50° C. In an aspect, grinding can be performed without raising the temperature of the cartilage above about 40° C. The temperature of the cartilage can be measured in any suitable manner. For example, thermocouples can be used to monitor the temperature of the cartilage directly, e.g., by measuring the temperature of the cartilage immediately after grinding, or indirectly, e.g., by measuring the temperature of the metal in the grinding mill. Continuous grinding in conventional grinding mills for 3-5 minutes can raise the temperature of the material to 70° C. or above. However, operating a grinding mill intermittently can preclude an undesirable rise in temperature. In an aspect, freeze-dried pieces of cartilage, 1-4 mm in size, can be ground in a grinding mill operating intermittently for 20-30 second intervals. After each grinding cycle, the cartilage can be sieved. The cartilage can be sieved through sieves of various sizes. Sieving can be used to separate cartilage into cartilage powder (i.e., particle sizes of less than 250 microns) and cartilage granules. Grinding can be repeated until the desired distribution of particles sizes can be obtained, such as, for example, from about 50 µm to about 900 µm. See, e.g., U.S. Pat. No. 8,318,212.

In an aspect, the disclosed bone microparticles can be prepared as follows. In an aspect, bone can be freeze-dried and processed, which can include repeated washing in warm saline or other balanced salt solutions to remove "undesirable constituents". In an aspect, the bone can be immersed directly into liquid nitrogen vapor and can then be freeze-dried to achieve a residual moisture of 5%-6% or less. Residual moisture content can be determined gravimetrically. In an aspect, freeze-dried bone can be cut into cubes with a band saw, an oscillating or a rotary saw without heating the bone preparation, by avoiding pressure on the bone being cut, and by limiting the time of grinding to no more than 15 second for each surface being cut. In an aspect, cut bone cubes, rectangles, or other small configurations can be further cut in a turbo mill, micro hammer cutter mill, disc mill, toothed disc mill, jet mill, or other similar mills to obtain particles of a smaller size. In an aspect, dry bone can be ground. Alternatively, in an aspect, wet bone preparation can be ground.

Heating bone above about 45° C. to about 50° C. can be undesirable as the heat can significantly reduce or can completely abolish osteoinductive properties of bone. For example, continuous grinding for 3 to 5 minutes in any of the conventional grinding mills can raise the temperature to 70° C. or above. Accordingly, in an aspect, a mill can be operated in cycles of about 8 seconds to about 18 seconds, then the bone can be sieved a duration of about 14 seconds to about 15 seconds. In an aspect, the temperature of bone or grinder can rise above about 33° C. from the initial temperature of the product (e.g., about 18° C. and about 20° C.). In an aspect, the cycle can operate for no longer than 3 minutes with an average operating time of about 2.5 minutes. In an aspect, after each grinding cycle, the bone can be sieved. In an aspect, the bone can be sieved through sieves of various sizes. Sieving can be used to separate bone into bone powder and bone granules. In an aspect, grinding can be repeated until the desired distribution of particles sizes can be obtained, such as, for example, from about 20 µm to about 800 µm. See, e.g., U.S. Pat. No. 7,335,381.

The term "contacting" as used herein refers to bringing a disclosed composition or bioactive implant together with an intended target (such as at least a portion of a bone or cartilage defect) or targeted area (such as an area diagnosed with, suspected of having, or susceptible to developing a bone or cartilage defect) in such a manner that the disclosed composition or bioactive implant can exert an effect on the intended target or targeted area either directly or indirectly. In an aspect, "contacting" means to insert or implant a bioactive implant at the site of a bone or cartilage defect.

The term "mixing" as used in a disclosed method of making a disclosed composition, for example, means to physically combine the recited components so as to achieve a homogenous solution. A person skilled in the art could ascertain without undue experimentation, the amount of time required to mix the recited components so as to achieve a solution.

As used herein, the term "determining" can refer to measuring or ascertaining the presence and severity of a bone or cartilage defect. Methods and techniques used to determining the presence and/or severity of a bone or cartilage defect are known to the medical arts. For example, the art is familiar with ways (e.g., radiograph, imaging (e.g., CT scan, MRI, etc.) to identify and/or diagnose the presence, severity, or both of a bone or cartilage defect.

As used herein, the terms "effective amount" and "amount effective" can refer to an amount that is sufficient to achieve the desired result such as, for example, the treatment and/or repair of a bone or cartilage defect. As used herein, the terms "effective amount" and "amount effective" can refer to an amount that is sufficient to achieve the desired an effect on an undesired condition (e.g., bone or cartilage defect). For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, then the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "autografts" are bone grafts that use bone obtained from the same subject that is receiving the graft. In an aspect, bone can be harvested from non-essential bones, such as the iliac crest or the fibula, the chin, the ribs, the mandible, and even parts of the skull. Autogenous bone possesses all the properties essential for bone formation. In other words, it is osteoconductive and osteoinductive, and it houses growth factors and osteogenic cells with no associated immune or infection related risks (i.e., non-immunogenic). Autologous bone fracts are slowly replaced by newly formed host bone. The disadvantages of autografts include possible post-operative pain and complications as well as blood loss, hematomas, infection, fracture, neurovascular injury, and cosmetic deformity at the explantation site. Autografts also require longer operative time. Moreover, the availability of an autogenous bone graft is limited in a pediatric subject or in an elderly subject as well as those subjects afflicted with osteopenia and osteoporosis.

As used herein, "allografts" can be derived from a subject other than the subject receiving the graft. Allograft bone can be collected from either living donors (e.g., patients receiving a total hip replacement surgery) or non-living donors. Allografts are typically processed by a bone tissue bank. An allograft can be osteoconductive and can be weakly osteoinductive. Processing an allograft can often require sterilization (i.e., gamma irradiation), which can detrimentally affect the mechanical properties of bone, and can deactivate proteins normally found in healthy bone.

As used herein, "xenografts" are bone grafts that originate in a species other than the species of the subject receiving the graft. For example, if subject is human, then a xenograft can be derived from a bovine bone or a porcine bone. In an aspect, the xenograft can be freeze-dried and/or demineralized and deproteinized.

Bone morphogenetic proteins (BMPs) are known to the art. As used herein, BMPs include, but are not limited to, BMP1, BMP2, BMP3, BMP4, BMP5, BMP6, BMP7, BMP8a, BMP8b, BMP10, and BMP15. BMPs exist at high concentration within bone and are secreted by many bone-forming cell types. Cellular signaling is an important function of BMPs. The art generally considers BMP2, BMP4, BMP6, and BMP7 to be the most osteoinductive of all known BMPs.

"Anti-fungal agents" are known to the art. As used herein, anti-fungal agents include, but are not limited to, abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

"Anti-bacterial agents" are known to the art. As used herein, anti-bacterial agents include, but are not limited to, afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. Anti-bacterial agents include quinolones, such as, for example, ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. Anti-bacterial agents include aminoglycosides such as, for example, amikacin, gentamicin, kanamycin, neomycin, streptomycin, tobramycin, or a combination thereof.

As used herein, "resorbable" refers to the ability of a material to be broken down over a period of time and assimilated into the biological environment.

As used herein, "embedded" refers to the physical relationship of the bone microparticles, cartilage microparticles, or both in a specific solution. In an aspect, "embed" means to fix an object, such as bone and cartilage microparticles, firmly and deeply in a surrounding mass, such as, for example, a desiccated solution.

As used herein, "biocompatible" refers to the ability of a composition or a bioactive implant disclosed herein to perform with an appropriate host response in a specific application, or at least to perform without having a toxic or otherwise deleterious effect on a biological system of the host (either locally or systemically).

As used herein, "biodegradable" refers to the ability of a composition or a bioactive implant disclosed herein to be degraded, disassembled, and/or digested over time by action of a biological environment (including the action of living organisms, e.g., the patient's body) and/or in response to a change in physiological pH or temperature.

As used herein, "osteoconductive" refers to the ability of a composition or a bioactive implant disclosed herein to passively permit bone growth (e.g., onto and/or into the composition or bioactive implant). As such, osteoconduction can be characterized as a passive process. A bioactive implant can be osteoconductive, for example, because it permits growth of bone on one or more surfaces. In an aspect, a bioactive implant disclosed herein can be osteoconductive.

As used herein, "osteoinductive" refers to the ability of a composition or a bioactive implant disclosed herein to actively stimulate a biological response that induces bone formation. As such, osteoinduction can be characterized as an active process. Osteoinduction can include, but is not limited to, the formation and/or stimulation of osteoprogenitor cells, such as osteoprogenitor cells, in bodily tissue surrounding or proximate to a bioactive implant. In an aspect, a bioactive implant disclosed herein can be osteoinductive.

As used herein, "demineralized bone matrix" (DBM) can be osteoconductive and osteoinductive. DBM retains much of the proteinaceous components native to bone, with small amounts of calcium-based solids, inorganic phosphates, and some trace cell debris. Many of these proteinaceous components (e.g., growth factors) are known to be potent osteogenic agents. DBM provides a degradable matrix facilitating endogenous release of these proteinaceous components at the site of a bone defect, thereby inducing new bone formation and accelerating healing.

As used herein, "demineralized" is intended to encompass such expressions as "substantially demineralized", "partially demineralized", "surface demineralized", and "fully demineralized." In an aspect, "partially demineralized" can encompass "surface demineralized".

In an aspect, a bone or cartilage defect can be, for example, a void, gap, or other defect in a bone or other bony structure in a body of a subject. For example, a defect can be in the spine, pelvis, an extremity, the cranium, or another bone or bony structure in the subject's body. In an aspect, a defect can include a site requiring bone, joint, cartilage, or ligament repair, construction, fusion, regeneration, or augmentation. The defect can be an osteochondral defect, such as an osteochondral plug. Such a defect traverses the entirety of the overlying cartilage and enters, at least in part, the underlying bony structure. In contrast, a chondral or subchondral defect traverses the overlying cartilage, in part or in whole, respectively, but does not involve the underlying bone. Other defects amenable to repair using the composition, bioactive implants, and methods disclosed herein include, but are not limited to, non-union fractures; bone cavities; tumor resection; fresh fractures (distracted or undistracted); cranial, maxillofacial and facial abnormalities, for example, in facial skeletal reconstruction, specifically, orbital floor reconstruction, augmentation of the alveolar ridge or sinus, periodontal defects and tooth extraction socket; cranioplasty, genioplasty, chin augmentation, palate reconstruction, and other large bony reconstructions; vertebroplasty, interbody fusions in the cervical, thoracic and lumbar spine and posteriolateral fusions in the thoracic and lumbar spine; in osteomyelitis for bone regeneration; appendicular fusion, ankle fusion, total hip, knee and joint fusions or arthroplasty; correcting tendon and/or ligamentous tissue defects such as, for example, the anterior, posterior, lateral and medial ligaments of the knee, the patella and Achilles tendons, and the like as well as those defects resulting from diseases such as cancer, arthritis, including osteoarthritis, and other bone degenerative disorders such as osteochondritis dessicans.

As used herein, "hydroxyethyl starch" (HES) is a derivative of amylopectin, which is a highly branched compound of starch. In humans and animals, amylopectin is rapidly hydrolyzed by amylase. Hydroxyethyl starches are identified by three numbers, e.g., 10% HES 200/0.5 or 6% HES 130/0.4. The first number indicates the concentration of the solution, the second represents the mean MW expressed in kiloDalton (kDa), and the third and most significant one is MS. These parameters are highly relevant to the pharmacokinetics of HES. See, e.g., Table 2.

collagen. In an aspect, collagen can include a combination of collagen from different species. In an aspect, collagen can be derived from several members of the same species. In an aspect, collagen can be collagen derived from human cartilage, human bone, or a combination thereof.

As used herein, "a desiccant" can be a substance that absorbs water. Desiccants are most commonly used to remove humidity that would normally degrade or even destroy products sensitive to moisture. Desiccants include, but are not limited to, activated alumina, aerogel, benzophenone, bentonite clay, calcium chloride, calcium sulfate, cobalt(ii) chloride, copper(ii) sulfate, lithium chloride, lithium bromide, magnesium sulfate, magnesium perchlorate, molecular sieve, potassium carbonate, silica gel, sodium, sodium chlorate, sodium chloride, sodium hydroxide, sodium sulfate, and sucrose.

Disclosed are the components to be used to prepare a composition or a bioactive implant disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually

TABLE 2

Characteristics of Various HES Preparations

| | Concentration and Solvent | Mean Molecular Weight, kDa | Molar Substitution | $C_2/C_6$ Ratio | Maximum Daily Dose, ml/kg |
|---|---|---|---|---|---|
| HES 670/0.75 | 6% balanced solution | 670 | 0.75 | 4.5:1 | 20 |
| HES 600/0.7 | 6% saline | 600 | 0.7 | 5:1 | 20 |
| HES 450/0.7 | 6% saline | 480 | 0.7 | 5:1 | 20 |
| HES 200/0.62 | 6% saline | 200 | 0.62 | 9:1 | 20 |
| HES 200/0.5 | 6% saline | 200 | 0.5 | 5:1 | 33 |
| | 10% saline | | | | 20 |
| HES 130/0.42 | 6% saline | 130 | 0.42 | 6:1 | 50 |
| HES 130/0.42 | 6% balanced solution | 130 | 0.42 | 6:1 | 50 |
| | 10% balanced solution | | | | 33 |
| HES 130/0.4 | 6% saline | 130 | 0.4 | 9:1 | 50 |
| | 10% saline | | | | 33 |
| HES 130/0.4 | 6% balanced solution | 130 | 0.4 | 9:1 | 50 |
| HES 70/0.5 | 6% balanced solution | 70 | 0.5 | 3:1 | 20 |

The FDA has approved HES products for the treatment and prophylaxis of hypovolemia: HESPAN (6% HES 450/0.7 in 0.9% Sodium Chloride Injection; B. Braun Medical Inc), Hetastarch (6% in 0.9% Sodium Chloride Injection, generic equivalent to HESPAN; Teva Pharmaceuticals USA), HEXTEND (6% HES 450/0.7 in physiological solution; BioTime Inc), and Voluven (6% HES 130/0.40 in normal saline; Fresenius Kabi USA, LLC).

As used herein, "collagen" can be or can include soluble collagen, insoluble collagen, or a combination thereof. In an aspect, collagen can be or can include type I collagen, type II collagen, type III collagen, type VII collagen, another suitable type of collagen, or a combination thereof. In an aspect, collagen can be human, equine, bovine, or porcine and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

B. Compositions

1. Compositions Comprising Bone Microparticles

Disclosed herein is a composition comprising bone microparticles in a solution, wherein the composition hardens upon desiccation into a bioactive implant. In an aspect, the hardened bioactive implant has a predetermined size and shape.

Disclosed herein is a composition comprising bone microparticles, wherein the size of the bone microparticles is from about 20 μm to about 800 μm.

Disclosed herein is a composition comprising bone microparticles in a hydroxyethyl starch solution, wherein the size of the bone microparticles is from about 20 μm to about 800 μm.

Disclosed herein is a composition comprising bone microparticles in a polyvinyl pyrrolidone (PVP) solution, wherein the size of the bone microparticles is from about 20 μm to about 800.

Disclosed herein is a composition comprising bone microparticles in a povidone iodine solution, wherein the size of the bone microparticles is from about 20 μm to about 800 μm.

Disclosed herein is a composition comprising bone microparticles in a collagen solution, wherein the size of the bone microparticles is from about 20 μm to about 800 μm.

Disclosed herein is a composition comprising bone microparticles in an albumin solution, wherein the size of the bone microparticles is from about 20 μm to about 800 μm.

In an aspect, a disclosed composition can be desiccated. In an aspect, a disclosed composition hardens upon desiccation into a bioactive implant. In an aspect, the hardened bioactive implant has a predetermined size and shape.

In an aspect, the bioactive implant can be osteogenic. In an aspect, the bioactive implant can have one or more smooth and even surfaces. In an aspect, the bioactive implant can have one or more rough and uneven surfaces. In an aspect, the rough and uneven surface can be pitted. In an aspect, the rough and uneven surfaces can facilitate vascular ingrowth.

In an aspect, the bioactive implant can be used in a spinal fusion, to treat or repair a maxillary defect, a mandibular defect, or both, to treat or repair a traumatic or a degenerative loss of bone, or both, to treat or repair a bone defect that follows a tumor resection, or a combination thereof. In an aspect, the bioactive implant can be used to treat or repair one or more of these defects or conditions.

In an aspect, the size of the bone microparticles in a disclosed composition can range from about 20 μm to about 100 μm, from about 100 μm to about 200 μm, from about 200 μm to about 300 μm, from about 300 μm to about 400 μm, from about 400 μm to about 500 μm, from about 500 μm to about 600 μm, from about 600 μm to about 700 μm, or from about 700 μm to about 800 μm.

In an aspect, the bone microparticles in a disclosed composition can be non-decalcified. In an aspect, the bone microparticles in a disclosed composition can be decalcified. In an aspect, the bone microparticles in a disclosed composition can comprise non-decalcified particles, decalcified particles, partially decalcified particles, demineralized bone matrix, or a combination thereof. In an aspect, a combination can comprise non-decalcified particles (NDP), decalcified particles (DP), partially decalcified particles (PDP), and demineralized bone matrix (DBM). In an aspect, a combination can comprise non-decalcified particles (NDP), decalcified particles (DP), and partially decalcified particles (PDP). In an aspect, a combination can comprise non-decalcified particles (NDP) and decalcified particles (DP). In an aspect, a combination can comprise non-decalcified particles (NDP) and partially decalcified particles (PDP). In an aspect, a combination can comprise non-decalcified particles (NDP) and demineralized bone matrix (DBM). In an aspect, a combination can comprise decalcified particles (DP) and partially decalcified particles (PDP). In an aspect, a combination can comprise decalcified particles (DP), partially decalcified particles (PDP), and demineralized bone matrix (DBM). In an aspect, a combination can comprise decalcified particles (DP) and demineralized bone matrix (DBM). In an aspect, a combination can comprise partially decalcified particles (PDP) and demineralized bone matrix (DBM). Table 1 provides a graphic representation of these various combinations.

TABLE 1

Listing of Various Combination of Types of Bone Microparticles

| | NDP | DP | PDP | DBM |
|---|---|---|---|---|
| 1 | X | X | X | X |
| 2 | X | X | X | |
| 3 | X | X | | |
| 4 | X | | X | |
| 5 | X | | | X |
| 6 | | X | X | |
| 7 | | X | X | X |
| 8 | | X | | X |
| 9 | | | X | X |

In an aspect, the amount of any one component (such as, for example, NDP, DP, PDP, or DMB) in a disclosed combination can range from about 1:1 to about 1:10 when compared to any other component. Alternatively, the amount of any one component (such as, for example, NDP, DP, PDP, or DMB) in a disclosed combination can range from about 1:10 to about 1:1 when compared to any other component. For example, the amount of one component (e.g., NDP microparticles) to a second component (e.g., DP microparticles) in a disclosed composition can be about 1:1, 1:2, 1:3, 1:4, 1:5, 1:6, 1:7, 1:8, 1:9, or 1:10, or 10:1, 9:1, 8:1, 7:1, 6:1, 5:1, 4:1, 3:1, or 2:1.

In an aspect, a disclosed composition can comprise about 10% to about 70% w/v of bone microparticles, or about 10% to about 35% w/v of bone microparticles, or about 25% w/v of bone microparticles, or about 50% w/v of bone microparticles.

In an aspect, the bone microparticles of a disclosed composition can be obtained from an allogeneic source, a syngeneic source, or an autogeneic source. In an aspect, an allogeneic source can be a cadaver. In an aspect, the bone microparticles can be obtained from one or more sources (i.e., one or more donors).

In an aspect, the solution of a disclosed composition can comprise hydroxyethyl starch. In an aspect, the solution of a disclosed composition can comprise non-solubilized hydroxyethyl starch. In an aspect, the solution of a disclosed composition can comprise about 6% hydroxyethyl starch. In an aspect, a HES solution can be converted into a putty, a gel, or a paste. In an aspect, the HES solution can be converted into a putty, a gel, or a paste via evaporation or the introduction of additional bone microparticles. In an aspect, the HES solution can be converted into a putty, a gel, or a paste via evaporation or the introduction of additional bone chips, shavings, or powder. In an aspect, a disclosed HES solution is non-toxic. In an aspect, a disclosed HES solution comprises non-toxic components. In an aspect, a disclosed HES solution is safe for administration to human beings or other mammals.

In an aspect, the solution of a disclosed composition can comprise polyvinyl pyrrolidone (PVP). In an aspect, the PVP can comprise various molecular weights. In an aspect, the PVP can have an average molecular weight of 40,000. PVPs are known to the skilled person in the art. In an aspect, a PVP solution can be converted into a putty, a gel, or a paste. In an aspect, the PVP solution can be converted into a putty, a gel, or a paste via evaporation or the introduction of additional bone microparticles. In an aspect, the PVP solution can be converted into a putty, a gel, or a paste via evaporation or the introduction of additional bone chips, shavings, or powder. In an aspect, a disclosed PVP solution is non-toxic. In an aspect, a disclosed PVP solution comprises non-toxic components. In an aspect, a disclosed PVP solution is safe for administration to human beings or other mammals.

In an aspect, the solution of a disclosed composition can comprise povidone iodine. In an aspect, a povidone iodine solution can be converted into a putty, a gel, or a paste. In an aspect, the povidone iodine solution can be converted into a putty, a gel, or a paste via evaporation or the introduction of additional bone microparticles. In an aspect, the povidone iodine solution can be converted into a putty, a gel, or a paste via evaporation or the introduction of additional bone chips, shavings, or powder. In an aspect, a disclosed povidone iodine solution is non-toxic. In an aspect, a disclosed povidone iodine solution comprises non-toxic components. In an aspect, a disclosed povidone iodine solution is safe for administration to human beings or other mammals.

In an aspect, the solution of a disclosed composition can comprise collagen. In an aspect, collagen can be tendon collagen, bone collagen, or a combination thereof. In an aspect, a collagen solution can be converted into a putty, a gel, or a paste. In an aspect, the collagen solution can be converted into a putty, a gel, or a paste via evaporation or the introduction of additional bone microparticles. In an aspect, the collagen solution can be converted into a putty, a gel, or a paste via evaporation or the introduction of additional bone chips, shavings, or powder. In an aspect, a disclosed collagen solution is non-toxic. In an aspect, a disclosed collagen solution comprises non-toxic components. In an aspect, a disclosed collagen solution is safe for administration to human beings or other mammals.

In an aspect, the solution of a disclosed composition can comprise albumin. In an aspect, albumin can be human albumin, recombinant albumin, bovine albumin, non-bovine albumin, egg albumin, transgenic albumin, or a combination thereof. In an aspect, an albumin solution can be converted into a putty, a gel, or a paste. In an aspect, the albumin solution can be converted into a putty, a gel, or a paste via evaporation or the introduction of additional bone microparticles. In an aspect, the albumin solution can be converted into a putty, a gel, or a paste via evaporation or the introduction of additional bone chips, shavings, or powder. In an aspect, a disclosed albumin solution is non-toxic. In an aspect, a disclosed albumin solution comprises non-toxic components. In an aspect, a disclosed albumin solution is safe for administration to human beings or other mammals.

In an aspect, a disclosed solution can comprise one or more of the following solutes: hydroxyethyl starch (HES), non-solubilized HES, polyvinyl pyrrolidone (PVP), povidone iodine, bone collagen, tendon collagen, and albumin (e.g., human albumin, recombinant albumin, bovine albumin, non-bovine albumin, egg albumin, transgenic albumin). In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed solution can comprise one or more of the following solutes: hydroxyethyl starch (HES), non-solubilized HES, polyvinyl pyrrolidone (PVP), povidone iodine, bone collagen, and tendon collagen, but not albumin. In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed composition can comprise one or more agents. In an aspect, the agents can comprise therapeutic agents, bone morphogenetic proteins, anti-infective agents (e.g., anti-microbial agents, anti-fungal agents, and combinations thereof), growth factors, growth hormones, antibiotics, antioxidants, analgesics, vitamins (e.g., vitamin D, vitamin K, and combinations thereof), sterilizing agents (e.g., iodine, bromine, calcium salts, and combinations thereof).

In an aspect, the solvent of a disclosed solution can comprise water. In an aspect, the solvent of a disclosed solution can comprise saline. In an aspect, the solvent of a disclosed solution can comprise DMSO. In an aspect, the solvent of a disclosed solution can comprise alcohol. In an aspect, the solvent of a disclosed solution can comprise a balanced salt solution. In an aspect, a balanced salt solution includes, but is not limited to, Hank's Balanced Salt Solution (HBSS), Earle's Balanced Salt Solution (EBSS), Phosphate-Buffered Saline (PBS), Dulbecco's Phosphate-Buffered Saline (DPBS), and combinations thereof.

In an aspect, the bone microparticles can be embedded evenly or embedded unevenly in the desiccated composition. In an aspect, the desiccated composition can comprise both evenly and unevenly embedded bone microparticles.

Disclosed herein is a composition comprising bone microparticles in a solution, wherein the size of the bone microparticles is from about 20 μm to about 800 μm, and wherein the composition hardens upon desiccation into a bioactive implant. In an aspect, the hardened bioactive implant has a predetermined size and shape.

Disclosed herein is a composition comprising bone microparticles in a hydroxyethyl starch solution, wherein the size of the bone microparticles is from about 20 μm to about 800 μm, and wherein the composition hardens upon desiccation into a bioactive implant. In an aspect, the hardened bioactive implant has a predetermined size and shape.

Disclosed herein is a composition comprising bone microparticles in a polyvinyl pyrrolidone (PVP) solution, wherein the size of the bone microparticles is from about 20 μm to about 800 μm, and wherein the composition hardens upon desiccation into a bioactive implant. In an aspect, the hardened bioactive implant has a predetermined size and shape.

Disclosed herein is a composition comprising bone microparticles in a povidone iodine solution, wherein the size of the bone microparticles is from about 20 μm to about 800 μm, and wherein the composition hardens upon desiccation into a bioactive implant. In an aspect, the hardened bioactive implant has a predetermined size and shape.

Disclosed herein is a composition comprising bone microparticles in a collagen solution, wherein the size of the bone microparticles is from about 20 μm to about 800 μm, and wherein the composition hardens upon desiccation into a bioactive implant. In an aspect, the hardened bioactive implant has a predetermined size and shape.

Disclosed herein is a composition comprising bone microparticles in an albumin solution, wherein the size of the bone microparticles is from about 20 μm to about 800 μm, and wherein the composition hardens upon desiccation into a bioactive implant. In an aspect, the hardened bioactive implant has a predetermined size and shape.

2. Compositions Comprising Cartilage Microparticles

Disclosed herein is a composition comprising cartilage microparticles in a solution, wherein the composition hardens upon desiccation into a bioactive implant. In an aspect, the hardened bioactive implant has a predetermined size and shape.

Disclosed herein is a composition comprising cartilage microparticles in a solution, wherein the size of the cartilage microparticles is from about 50 μm to about 900 μm.

Disclosed herein is a composition comprising cartilage microparticles in a hydroxyethyl starch solution, wherein the size of the cartilage microparticles is from about 50 μm to about 900 μm.

Disclosed herein is a composition comprising cartilage microparticles in a polyvinyl pyrrolidone (PVP) solution, wherein the size of the cartilage microparticles is from about 50 μm to about 900 μm.

Disclosed herein is a composition comprising cartilage microparticles in a povidone iodine solution, wherein the size of the cartilage microparticles is from about 50 μm to about 900 μm.

Disclosed herein is a composition comprising cartilage microparticles in a collagen solution, wherein the size of the cartilage microparticles is from about 50 μm to about 900 μm.

Disclosed herein is a composition comprising cartilage microparticles in an albumin solution, wherein the size of the cartilage microparticles is from about 50 μm to about 900 μm.

In an aspect, a disclosed composition can be desiccated. In an aspect, a disclosed composition hardens upon desiccation into bioactive implant. In an aspect, the hardened bioactive implant has a predetermined size and shape.

In an aspect, the bioactive implant can be chondrogenic. In an aspect, the bioactive implant can have one or more smooth and even surfaces. In an aspect, the bioactive implant can have one or more rough and uneven surfaces. In an aspect, the rough and uneven surface can be pitted. In an aspect, the rough and uneven surfaces can facilitate vascular ingrowth.

In an aspect, the bioactive implant can be to treat or repair a traumatic loss or a degenerative loss of cartilage, or both, to treat or repair a cartilage defect following a tumor resection, to treat or repair a degenerative chondrol lesion, a traumatic chondral lesion, or both, or a combination thereof. In an aspect, the bioactive implant can be used to treat or repair one or more of these defects or conditions.

In an aspect, the size of the cartilage microparticles in a disclosed composition can range from about 50 μm to about 100 μm, from about 100 μm to about 150 μm, from about 150 μm to about 200 μm, from about 200 μm to about 250 μm, from about 250 μm to about 300 μm, from about 300 μm to about 350 μm, from about 350 μm to about 400 μm, from about 400 μm to about 450 μm, from about 450 μm to about 500 μm, from about 500 μm to about 550 μm, from about 550 μm to about 600 μm, from about 600 μm to about 650 μm, from about 650 μm to about 700 μm, from about 700 μm to about 750 μm, from about 750 μm to about 800 μm, from about 800 μm to about 850 μm, or from about 850 μm to about 900 μm.

In an aspect, the cartilage microparticles in a disclosed composition can be non-decalcified. In an aspect, the cartilage microparticles in a disclosed composition can be decalcified.

In an aspect, a disclosed composition can comprise about 10% to about 70% w/v of cartilage microparticles, or about 10% to about 35% w/v of cartilage microparticles, or about 25% w/v of cartilage microparticles, or about 50% w/v of cartilage microparticles.

In an aspect, the cartilage microparticles of a disclosed composition can be obtained from an allogeneic source, a syngeneic source, or an autogeneic source. In an aspect, an allogeneic source can be a cadaver. In an aspect, the cartilage microparticles can be obtained from one or more sources (i.e., one or more donors).

In an aspect, the solution of a disclosed composition can comprise hydroxyethyl starch. In an aspect, the solution of a disclosed composition can comprise non-solubilized hydroxyethyl starch. In an aspect, the solution of a disclosed composition can comprise about 6% hydroxyethyl starch. In an aspect, a HES solution can be converted into a putty, a gel, or a paste. In an aspect, the HES solution can be converted into a putty, a gel, or a paste via evaporation or the introduction of cartilage microparticles. In an aspect, the HES solution can be converted into a putty, a gel, or a paste via evaporation or the introduction of additional cartilage chips, shavings, or powder. In an aspect, a disclosed HES solution is non-toxic. In an aspect, a disclosed HES solution comprises non-toxic components. In an aspect, a disclosed HES solution is safe for administration to human beings or other mammals.

In an aspect, the solution of a disclosed composition can comprise polyvinyl pyrrolidone (PVP). In an aspect, the PVP can comprise various molecular weights. In an aspect, the PVP can have an average molecular weight of 40,000. PVPs are known to the skilled person in the art. In an aspect, a PVP solution can be converted into a putty, a gel, or a paste. In an aspect, the PVP solution can be converted into a putty, a gel, or a paste via evaporation or the introduction of additional cartilage microparticles. In an aspect, the PVP solution can be converted into a putty, a gel, or a paste via evaporation or the introduction of additional cartilage chips, shavings, or powder. In an aspect, a disclosed PVP solution is non-toxic. In an aspect, a disclosed PVP solution comprises non-toxic components. In an aspect, a disclosed PVP solution is safe for administration to human beings or other mammals.

In an aspect, the solution of a disclosed composition can comprise povidone iodine. In an aspect, a povidone iodine solution can be converted into a putty, a gel, or a paste. In an aspect, the povidone iodine solution can be converted into a putty, a gel, or a paste via evaporation or the introduction of additional cartilage microparticles. In an aspect, the povidone iodine solution can be converted into a putty, a gel, or a paste via evaporation or the introduction of additional cartilage chips, shavings, or powder. In an aspect, a disclosed povidone iodine solution is non-toxic. In an aspect, a disclosed povidone iodine solution comprises non-toxic components. In an aspect, a disclosed povidone iodine solution is safe for administration to human beings or other mammals.

In an aspect, the solution of a disclosed composition can comprise collagen. In an aspect, collagen can be tendon collagen, bone collagen, or a combination thereof. In an aspect, a collagen solution can be converted into a putty, a gel, or a paste. In an aspect, the collagen solution can be converted into a putty, a gel, or a paste via evaporation or the introduction of additional cartilage microparticles. In an aspect, the collagen solution can be converted into a putty, a gel, or a paste via evaporation or the introduction of additional cartilage chips, shavings, or powder. In an aspect, a disclosed collagen solution is non-toxic. In an aspect, a disclosed collagen solution comprises non-toxic components. In an aspect, a disclosed collagen solution is safe for administration to human beings or other mammals.

In an aspect, the solution of a disclosed composition can comprise albumin. In an aspect, albumin can be human albumin, recombinant albumin, bovine albumin, non-bovine albumin, egg albumin, transgenic albumin, or a combination thereof. In an aspect, an albumin solution can be converted into a putty, a gel, or a paste. In an aspect, the albumin solution can be converted into a putty, a gel, or a paste via evaporation or the introduction of additional cartilage microparticles. In an aspect, the albumin solution can be converted into a putty, a gel, or a paste via evaporation or the introduction of additional cartilage chips, shavings, or powder. In an aspect, a disclosed albumin solution is non-toxic. In an aspect, a disclosed albumin solution comprises non-toxic components. In an aspect, a disclosed albumin solution is safe for administration to human beings or other mammals.

In an aspect, a disclosed solution can comprise one or more of the following solutes: hydroxyethyl starch (HES), non-solubilized HES, polyvinyl pyrrolidone (PVP), povidone iodine, bone collagen, tendon collagen, and albumin (e.g., human albumin, recombinant albumin, bovine albumin, non-bovine albumin, egg albumin, transgenic albumin). In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed solution can comprise one or more of the following solutes: hydroxyethyl starch (HES), non-solubilized HES, polyvinyl pyrrolidone (PVP), povidone iodine, bone collagen, and tendon collagen, but not albumin. In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed composition can comprise one or more agents. In an aspect, the agents can comprise therapeutic agents, bone morphogenetic proteins, anti-infective agents (e.g., anti-microbial agents, anti-fungal agents, and combinations thereof), growth factors, growth hormones, antibiotics, antioxidants, analgesics, vitamins (e.g., vitamin D, vitamin K, and combinations thereof), sterilizing agents (e.g., iodine, bromine, calcium salts, and combinations thereof).

In an aspect, the solvent of a disclosed solution can comprise water. In an aspect, the solvent of a disclosed solution can comprise saline. In an aspect, the solvent of a disclosed solution can comprise DMSO. In an aspect, the solvent of a disclosed solution can comprise alcohol. In an aspect, the solvent of a disclosed solution can comprise a balanced salt solution. In an aspect, a balanced salt solution includes, but is not limited to, Hank's Balanced Salt Solution (HBSS), Earle's Balanced Salt Solution (EBSS), Phosphate-Buffered Saline (PBS), Dulbecco's Phosphate-Buffered Saline (DPBS), and combinations thereof.

In an aspect, the cartilage microparticles can be embedded evenly or embedded unevenly in the desiccated composition. In an aspect, the desiccated composition can comprise both evenly and unevenly embedded cartilage microparticles.

Disclosed herein is a composition comprising cartilage microparticles in a solution, wherein the size of the cartilage microparticles is from about 50 μm to about 900 μm, and wherein the composition hardens upon desiccation into a bioactive implant. In an aspect, the hardened bioactive implant has a predetermined size and shape.

Disclosed herein is a composition comprising cartilage microparticles in a hydroxyethyl starch solution, wherein the size of the cartilage microparticles is from about 50 μm to about 900 μm, and wherein the composition hardens upon desiccation into a bioactive implant. In an aspect, the hardened bioactive implant has a predetermined size and shape.

Disclosed herein is a composition comprising cartilage microparticles in a polyvinyl pyrrolidone (PVP) solution, wherein the size of the cartilage microparticles is from about 50 μm to about 900 μm, and wherein the composition hardens upon desiccation into a bioactive implant. In an aspect, the hardened bioactive implant has a predetermined size and shape.

Disclosed herein is a composition comprising cartilage microparticles in a povidone iodine solution, wherein the size of the cartilage microparticles is from about 50 μm to about 900 μm, and wherein the composition hardens upon desiccation into a bioactive implant. In an aspect, the hardened bioactive implant has a predetermined size and shape.

Disclosed herein is a composition comprising cartilage microparticles in a collagen solution, wherein the size of the cartilage microparticles is from about 50 μm to about 900 μm, and wherein the composition hardens upon desiccation into a bioactive implant. In an aspect, the hardened bioactive implant has a predetermined size and shape.

Disclosed herein is a composition comprising cartilage microparticles in an albumin solution, wherein the size of the cartilage microparticles is from about 50 μm to about 900 μm, and wherein the composition hardens upon desiccation into a bioactive implant. In an aspect, the hardened bioactive implant has a predetermined size and shape.

3. Product by Process for Compositions Comprising Bone Microparticles

Disclosed herein is a bioactive implant made by a method comprising desiccating a composition disclosed herein.

Disclosed herein is a bioactive implant made by a method comprising desiccating a composition comprising bone microparticles in a solution.

Disclosed herein is a bioactive implant made by a method comprising desiccating a composition comprising bone microparticles in a solution, wherein the size of the bone microparticles is from about 20 μm to about 800 μm.

Disclosed herein is a bioactive implant made by a method comprising desiccating a composition comprising bone microparticles in a hydroxyethyl starch solution, wherein the size of the bone microparticles is from about 20 μm to about 800 μm.

Disclosed herein is a bioactive implant made by a method comprising adding to a mold a disclosed composition and desiccating the composition.

Disclosed herein is a bioactive implant made by a method comprising adding to a mold a composition comprising bone microparticles in a solution and desiccating the composition.

Disclosed herein is a bioactive implant made by a method comprising preparing a composition comprising bone microparticles in a solution; adding to a mold the composition; and desiccating the composition.

Disclosed herein is a bioactive implant made by a method comprising adding to a mold a composition comprising bone microparticles in a solution, wherein the size of the bone microparticles is from about 20 μm to about 800 μm; and desiccating the composition.

Disclosed herein is a bioactive implant made by a method comprising preparing a composition comprising bone microparticles in a solution, wherein the size of the bone microparticles is from about 20 μm to about 800 μm; adding to a mold the composition; and desiccating the composition.

In an aspect, desiccating comprises producing a hardened bioactive implant having a predetermined size and shape.

In an aspect, the method can comprise preparing the composition.

In an aspect, the method can comprise adding to a mold the composition.

In an aspect, the at least one mold can have a volume from about 1 mL to about 120 mL. In an aspect, the at least one mold can have a volume from about 500 mL to about 2000 mL. In an aspect, the at least one mold can have a volume greater than 2000 mL. In an aspect, a mold can be customized for a specific bone defect or bone defects of the subject.

In an aspect, the size of the bone microparticles in a disclosed composition can range from about 20 μm to about 100 μm, from about 100 μm to about 200 μm, from about 200 μm to about 300 μm, from about 300 μm to about 400 μm, from about 400 μm to about 500 μm, from about 500 μm to about 600 μm, from about 600 μm to about 700 μm, or from about 700 μm to about 800 μm.

In an aspect, the disclosed composition can comprise about 10% to about 70% w/v of bone microparticles, or about 10% to about 35% w/v of bone microparticles, or about 25% w/v of bone microparticles, or about 50% w/v of bone microparticles.

In an aspect, desiccating the composition can occur in a vacuum. In an aspect, the vacuum can measure at about 400 millitorr or less. In an aspect, the vacuum can measure at about 300 millitorr or less. In an aspect, the vacuum can measure at about 200 millitorr or less. In an aspect, the vacuum can measure at about 100 millitorr or less.

In an aspect, desiccating the composition can comprise freeze-drying the composition. In an aspect, freeze-drying can comprise an amount of time from about 24 hours to about 120 hours. For example, in an aspect, freeze-drying can comprise 24 hours, 48 hours, 72 hours, 96 hours, or 120 hours, or some amount of time between 24 and 48 hours, between 48 and 72 hours, between 72 and 96 hours, or between 96 and 120 hours.

In an aspect, freeze-drying can occur at a temperature from about −40° C. to about −80° C. For example, in an aspect, freeze-drying can occur at −40° C., −50° C., −60° C., −70° C., or −80° C., or at some temperature between −40° C. and −50° C., −50° C. and −60° C., −60° C. and −70° C., or −70° C. and −80° C.

In an aspect, desiccating the composition can comprise subjecting the composition to hypothermic dehydration. In an aspect, hypothermic dehydration can occur at a temperature from about 2° C. to about 10° C. In an aspect, for example, hypothermic dehydration can occur at 2° C., 3° C., 4° C., 5° C., 6° C., 7° C., 8° C., 9° C., or 10° C., or at some temperature between 2° C. and 3° C., 3° C. and 4° C., 4° C. and 5° C., 5° C. and 6° C., 6° C. and 7° C., 7° C. and 8° C., 8° C. and 9° C., or 9° C. and 10° C. In an aspect, hypothermic dehydration can comprise an amount of time from about 24 to about 72 hours. For example, in an aspect, hypothermic dehydration can occur 24 hours, 48 hours, or 72 hours, or some amount of time between 24 and 48 hours or between 48 and 72 hours.

In an aspect, the bioactive implant can be osteogenic. In an aspect, the bioactive implant can have one or more smooth and even surfaces. In an aspect, the bioactive implant can have one or more rough and uneven surfaces. In an aspect, the rough and uneven surface can be pitted. In an aspect, the rough and uneven surfaces can facilitate vascular ingrowth.

In an aspect, the bioactive implant made by the disclosed method can be used in a spinal fusion, to treat or repair a maxillary defect, a mandibular defect, or both, to treat or repair a traumatic or a degenerative loss of bone, or both, to treat or repair a bone defect that follows a tumor resection, or a combination thereof. In an aspect, the bioactive implant can be used to treat or repair one or more of these defects or conditions.

In an aspect, the solution of a disclosed composition can comprise hydroxyethyl starch. In an aspect, the solution of a disclosed composition can comprise non-solubilized hydroxyethyl starch. In an aspect, the solution of a disclosed composition can comprise about 6% hydroxyethyl starch. In an aspect, a HES solution can be converted into a putty, a gel, or a paste. In an aspect, the HES solution can be converted into a putty, a gel, or a paste via evaporation or the introduction of additional bone microparticles. In an aspect, the HES solution can be converted into a putty, a gel, or a paste via evaporation or the introduction of additional bone chips, shavings, or powder. In an aspect, a disclosed HES solution is non-toxic. In an aspect, a disclosed HES solution comprises non-toxic components. In an aspect, a disclosed HES solution is safe for administration to human beings or other mammals.

In an aspect, the solution of a disclosed composition can comprise polyvinyl pyrrolidone (PVP). In an aspect, the PVP can comprise various molecular weights. In an aspect, the PVP can have an average molecular weight of 40,000. PVPs are known to the skilled person in the art. In an aspect, a PVP solution can be converted into a putty, a gel, or a paste. In an aspect, the PVP solution can be converted into a putty, a gel, or a paste via evaporation or the introduction of additional bone microparticles. In an aspect, the PVP solution can be converted into a putty, a gel, or a paste via evaporation or the introduction of additional bone chips, shavings, or powder. In an aspect, a disclosed PVP solution is non-toxic. In an aspect, a disclosed PVP solution comprises non-toxic components. In an aspect, a disclosed PVP solution is safe for administration to human beings or other mammals.

In an aspect, the solution of a disclosed composition can comprise povidone iodine. In an aspect, a povidone iodine solution can be converted into a putty, a gel, or a paste. In an aspect, the povidone iodine solution can be converted into a putty, a gel, or a paste via evaporation or the introduction of additional bone microparticles. In an aspect, the povidone iodine solution can be converted into a putty, a gel, or a paste via evaporation or the introduction of additional bone chips, shavings, or powder. In an aspect, a disclosed povidone iodine solution is non-toxic. In an aspect, a disclosed povidone iodine solution comprises non-toxic components. In an aspect, a disclosed povidone iodine solution is safe for administration to human beings or other mammals.

In an aspect, the solution of a disclosed composition can comprise collagen. In an aspect, collagen can be tendon collagen, bone collagen, or a combination thereof. In an aspect, a collagen solution can be converted into a putty, a gel, or a paste. In an aspect, the collagen solution can be converted into a putty, a gel, or a paste via evaporation or the introduction of additional bone microparticles. In an aspect, the collagen solution can be converted into a putty, a gel, or a paste via evaporation or the introduction of additional bone chips, shavings, or powder. In an aspect, a disclosed collagen solution is non-toxic. In an aspect, a disclosed collagen solution comprises non-toxic components. In an aspect, a disclosed collagen solution is safe for administration to human beings or other mammals.

In an aspect, the solution of a disclosed composition can comprise albumin. In an aspect, albumin can be human albumin, recombinant albumin, bovine albumin, non-bovine albumin, egg albumin, transgenic albumin, or a combination thereof. In an aspect, an albumin solution can be converted into a putty, a gel, or a paste. In an aspect, the albumin solution can be converted into a putty, a gel, or a paste via evaporation or the introduction of additional bone microparticles. In an aspect, the albumin solution can be converted into a putty, a gel, or a paste via evaporation or the introduction of additional bone chips, shavings, or powder. In an aspect, a disclosed albumin solution is non-toxic. In an aspect, a disclosed albumin solution comprises non-toxic components. In an aspect, a disclosed albumin solution is safe for administration to human beings or other mammals.

In an aspect, a disclosed solution can comprise one or more of the following solutes: hydroxyethyl starch (HES), non-solubilized HES, polyvinyl pyrrolidone (PVP), povidone iodine, bone collagen, tendon collagen, and albumin (e.g., human albumin, recombinant albumin, bovine albumin, non-bovine albumin, egg albumin, transgenic albumin). In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed solution can comprise one or more of the following solutes: hydroxyethyl starch (HES), non-solubilized HES, polyvinyl pyrrolidone (PVP), povidone iodine, bone collagen, and tendon collagen, but not albumin. In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, the bone microparticles can be embedded evenly or embedded unevenly in the desiccated composition. In an aspect, the desiccated composition can comprise both evenly and unevenly embedded bone microparticles.

Disclosed herein is a bioactive implant made by a method comprising desiccating a composition comprising bone microparticles in a polyvinyl pyrrolidone (PVP) solution, wherein the size of the bone microparticles is from about 20 µm to about 800 µm. In an aspect, desiccating comprises producing a hardened bioactive implant having a predetermined size and shape.

Disclosed herein is a bioactive implant made by a method comprising desiccating a composition comprising bone microparticles in a povidone iodine solution, wherein the size of the bone microparticles is from about 20 μm to about 800 μm. In an aspect, desiccating comprises producing a hardened bioactive implant having a predetermined size and shape.

Disclosed herein is a bioactive implant made by a method comprising desiccating a composition comprising bone microparticles in a collagen solution, wherein the size of the bone microparticles is from about 20 μm to about 800 μm. In an aspect, desiccating comprises producing a hardened bioactive implant having a predetermined size and shape.

Disclosed herein is a bioactive implant made by a method comprising desiccating a composition comprising bone microparticles in an albumin solution, wherein the size of the bone microparticles is from about 20 μm to about 800 μm. In an aspect, desiccating comprises producing a hardened bioactive implant having a predetermined size and shape.

4. Product by Process for Compositions Comprising Cartilage Microparticles

Disclosed herein is a bioactive implant made by a method comprising desiccating a composition disclosed herein.

Disclosed herein is a bioactive implant made by a method comprising desiccating a composition comprising cartilage microparticles in a solution.

Disclosed herein is a bioactive implant made by a method comprising desiccating a composition comprising cartilage microparticles in a solution, wherein the size of the cartilage microparticles is from about 50 μm to about 900 μm.

Disclosed herein is a bioactive implant made by a method comprising desiccating a composition comprising cartilage microparticles in a hydroxyethyl starch solution, wherein the size of the cartilage microparticles is from about 50 μm to about 900 μm.

Disclosed herein is a bioactive implant made by a method comprising adding to a mold a disclosed composition and desiccating the composition.

Disclosed herein is a bioactive implant made by a method comprising adding to a mold a composition comprising cartilage microparticles in a solution and desiccating the composition.

Disclosed herein is a bioactive implant made by a method comprising preparing a composition comprising cartilage microparticles in a solution; adding to a mold the composition; and desiccating the composition.

Disclosed herein is a bioactive implant made by a method comprising adding to a mold a composition comprising cartilage microparticles in a solution, wherein the size of the cartilage microparticles is from about 50 μm to about 900 μm; and desiccating the composition.

Disclosed herein is a bioactive implant made by a method comprising preparing a composition comprising cartilage microparticles in a solution, wherein the size of the cartilage microparticles is from about 50 μm to about 900 μm; adding to a mold the composition; and desiccating the composition.

In an aspect, desiccating comprises producing a hardened bioactive implant having a predetermined size and shape.

In an aspect, the method can comprise preparing the composition.

In an aspect, the method can comprise adding to a mold the composition.

In an aspect, the at least one mold can have a volume from about 1 mL to about 120 mL. In an aspect, the at least one mold can have a volume from about 500 mL to about 2000 mL. In an aspect, the at least one mold can have a volume greater than 2000 mL. In an aspect, a mold can be customized for a specific cartilage defect or cartilage defects of the subject.

In an aspect, the size of the cartilage microparticles can range from about 50 μm to about 100 μm, from about 100 μm to about 150 μm, from about 150 μm to about 200 μm, from about 200 μm to about 250 μm, from about 250 μm to about 300 μm, from about 300 μm to about 350 μm, from about 350 μm to about 400 μm, from about 400 μm to about 450 μm, from about 450 μm to about 500 μm, from about 500 μm to about 550 μm, from about 550 μm to about 600 μm, from about 600 μm to about 650 μm, from about 650 μm to about 700 μm, from about 700 μm to about 750 μm, from about 750 μm to about 800 μm, from about 800 μm to about 850 μm, or from about 850 μm to about 900 μm.

In an aspect, the disclosed composition can comprise about 10% to about 70% w/v of cartilage microparticles, or about 10% to about 35% w/v of cartilage microparticles, or about 25% w/v of cartilage microparticles, or about 50% w/v of cartilage microparticles.

In an aspect, desiccating the composition can occur in a vacuum. In an aspect, the vacuum can measure at about 400 millitorr or less. In an aspect, the vacuum can measure at about 300 millitorr or less. In an aspect, the vacuum can measure at about 200 millitorr or less. In an aspect, the vacuum can measure at about 100 millitorr or less.

In an aspect, desiccating the composition can comprise freeze-drying the composition. In an aspect, freeze-drying can comprise an amount of time from about 24 hours to about 120 hours. For example, in an aspect, freeze-drying can comprise 24 hours, 48 hours, 72 hours, 96 hours, or 120 hours, or some amount of time between 24 and 48 hours, between 48 and 72 hours, between 72 and 96 hours, or between 96 and 120 hours.

In an aspect, freeze-drying can occur at a temperature from about −40° C. to about −80° C. For example, in an aspect, freeze-drying can occur at −40° C., −50° C., −60° C., −70° C., or −80° C., or at some temperature between −40° C. and −50° C., −50° C. and −60° C., −60° C. and −70° C., or −70° C. and −80° C.

In an aspect, desiccating the composition can comprise subjecting the composition to hypothermic dehydration. In an aspect, hypothermic dehydration can occur at a temperature from about 2° C. to about 10° C. In an aspect, for example, hypothermic dehydration can occur at 2° C., 3° C., 4° C., 5° C., 6° C., 7° C., 8° C., 9° C., or 10° C., or at some temperature between 2° C. and 3° C., 3° C. and 4° C., 4° C. and 5° C., 5° C. and 6° C., 6° C. and 7° C., 7° C. and 8° C., 8° C. and 9° C., or 9° C. and 10° C. In an aspect, hypothermic dehydration can comprise an amount of time from about 24 to about 72 hours. For example, in an aspect, hypothermic dehydration can occur 24 hours, 48 hours, or 72 hours, or some amount of time between 24 and 48 hours or between 48 and 72 hours.

In an aspect, the bioactive implant can be chondrogenic. In an aspect, the bioactive implant can have one or more smooth and even surfaces. In an aspect, the bioactive implant can have one or more rough and uneven surfaces. In an aspect, the rough and uneven surface can be pitted. In an aspect, the rough and uneven surfaces can facilitate vascular ingrowth.

In an aspect, the bioactive implant can be to treat or repair a traumatic loss or a degenerative loss of cartilage, or both, to treat or repair a cartilage defect following a tumor resection, to treat or repair a degenerative chondrol lesion, a traumatic chondral lesion, or both, or a combination thereof.

In an aspect, the bioactive implant can be used to treat or repair one or more of these defects or conditions.

In an aspect, the solution of a disclosed composition can comprise hydroxyethyl starch. In an aspect, the solution of a disclosed composition can comprise non-solubilized hydroxyethyl starch. In an aspect, the solution of a disclosed composition can comprise about 6% hydroxyethyl starch. In an aspect, a HES solution can be converted into a putty, a gel, or a paste. In an aspect, the HES solution can be converted into a putty, a gel, or a paste via evaporation or the introduction of cartilage microparticles. In an aspect, the HES solution can be converted into a putty, a gel, or a paste via evaporation or the introduction of additional cartilage chips, shavings, or powder. In an aspect, a disclosed HES solution is non-toxic. In an aspect, a disclosed HES solution comprises non-toxic components. In an aspect, a disclosed HES solution is safe for administration to human beings or other mammals.

In an aspect, the solution of a disclosed composition can comprise polyvinyl pyrrolidone (PVP). In an aspect, the PVP can comprise various molecular weights. In an aspect, the PVP can have an average molecular weight of 40,000. PVPs are known to the skilled person in the art. In an aspect, a PVP solution can be converted into a putty, a gel, or a paste. In an aspect, the PVP solution can be converted into a putty, a gel, or a paste via evaporation or the introduction of additional cartilage microparticles. In an aspect, the PVP solution can be converted into a putty, a gel, or a paste via evaporation or the introduction of additional cartilage chips, shavings, or powder. In an aspect, a disclosed PVP solution is non-toxic. In an aspect, a disclosed PVP solution comprises non-toxic components. In an aspect, a disclosed PVP solution is safe for administration to human beings or other mammals.

In an aspect, the solution of a disclosed composition can comprise povidone iodine. In an aspect, a povidone iodine solution can be converted into a putty, a gel, or a paste. In an aspect, the povidone iodine solution can be converted into a putty, a gel, or a paste via evaporation or the introduction of additional cartilage microparticles. In an aspect, the povidone iodine solution can be converted into a putty, a gel, or a paste via evaporation or the introduction of additional cartilage chips, shavings, or powder. In an aspect, a disclosed povidone iodine solution is non-toxic. In an aspect, a disclosed povidone iodine solution comprises non-toxic components. In an aspect, a disclosed povidone iodine solution is safe for administration to human beings or other mammals.

In an aspect, the solution of a disclosed composition can comprise collagen. In an aspect, collagen can be tendon collagen, bone collagen, or a combination thereof. In an aspect, a collagen solution can be converted into a putty, a gel, or a paste. In an aspect, the collagen solution can be converted into a putty, a gel, or a paste via evaporation or the introduction of additional cartilage microparticles. In an aspect, the collagen solution can be converted into a putty, a gel, or a paste via evaporation or the introduction of additional cartilage chips, shavings, or powder. In an aspect, a disclosed collagen solution is non-toxic. In an aspect, a disclosed collagen solution comprises non-toxic components. In an aspect, a disclosed collagen solution is safe for administration to human beings or other mammals.

In an aspect, the solution of a disclosed composition can comprise albumin. In an aspect, albumin can be human albumin, recombinant albumin, bovine albumin, non-bovine albumin, egg albumin, transgenic albumin, or a combination thereof. In an aspect, an albumin solution can be converted into a putty, a gel, or a paste. In an aspect, the albumin solution can be converted into a putty, a gel, or a paste via evaporation or the introduction of additional cartilage microparticles. In an aspect, the albumin solution can be converted into a putty, a gel, or a paste via evaporation or the introduction of additional cartilage chips, shavings, or powder. In an aspect, a disclosed albumin solution is non-toxic. In an aspect, a disclosed albumin solution comprises non-toxic components. In an aspect, a disclosed albumin solution is safe for administration to human beings or other mammals.

In an aspect, a disclosed solution can comprise one or more of the following solutes: hydroxyethyl starch (HES), non-solubilized HES, polyvinyl pyrrolidone (PVP), povidone iodine, bone collagen, tendon collagen, and albumin (e.g., human albumin, recombinant albumin, bovine albumin, non-bovine albumin, egg albumin, transgenic albumin). In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed solution can comprise one or more of the following solutes: hydroxyethyl starch (HES), non-solubilized HES, polyvinyl pyrrolidone (PVP), povidone iodine, bone collagen, and tendon collagen, but not albumin. In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, the cartilage microparticles can be embedded evenly or embedded unevenly in the desiccated composition. In an aspect, the desiccated composition can comprise both evenly and unevenly embedded cartilage microparticles.

Disclosed herein is a bioactive implant made by a method comprising desiccating a composition comprising cartilage microparticles in a polyvinyl pyrrolidone (PVP) solution, wherein the size of the cartilage microparticles is from about 50 μm to about 900 μm. In an aspect, desiccating comprises producing a hardened bioactive implant having a predetermined size and shape.

Disclosed herein is a bioactive implant made by a method comprising desiccating a composition comprising cartilage microparticles in a povidone iodine solution, wherein the size of the cartilage microparticles is from about 50 µm to about 900 µm. In an aspect, desiccating comprises producing a hardened bioactive implant having a predetermined size and shape.

Disclosed herein is a bioactive implant made by a method comprising desiccating a composition comprising cartilage microparticles in a collagen solution, wherein the size of the cartilage microparticles is from about 50 µm to about 900 µm. In an aspect, desiccating comprises producing a hardened bioactive implant having a predetermined size and shape.

Disclosed herein is a bioactive implant made by a method comprising desiccating a composition comprising cartilage microparticles in an albumin solution, wherein the size of the cartilage microparticles is from about 50 µm to about 900 µm. In an aspect, desiccating comprises producing a hardened bioactive implant having a predetermined size and shape.

5. Containers

Disclosed herein is a container comprising a composition disclosed herein.

Disclosed herein is a container comprising a composition, wherein the composition comprises bone microparticles in a solution.

Disclosed herein is a container comprising a composition, wherein the composition comprises cartilage microparticles in a solution.

Disclosed herein is a container comprising a composition, wherein the composition comprises bone microparticles in a solution, wherein the size of the bone microparticles is from about 20 µm to about 800.

Disclosed herein is a container comprising a composition, wherein the composition comprises cartilage microparticles in a solution, wherein the size of the cartilage microparticles is from about 50 µm to about 900 µm.

Disclosed herein is a container comprising a composition comprising bone microparticles in a solution, wherein the size of the bone microparticles is from about 20 µm to about 800 µm, and wherein the composition hardens upon desiccation into a bioactive implant. In an aspect, the hardened bioactive implant has a predetermined size and shape.

Disclosed herein is a container comprising a composition comprising cartilage microparticles in a solution, wherein the size of the cartilage microparticles is from about 50 µm to about 900 µm, and wherein the composition hardens upon desiccation into a bioactive implant. In an aspect, the hardened bioactive implant has a predetermined size and shape.

In an aspect, a disclosed container can be sterilized. In an aspect, a disclosed container can be autoclaved.

In an aspect, a disclosed container does not contribute to the degradation of the composition contained therein. In an aspect of a disclosed contain, the composition contained therein can harden upon desiccation into a bioactive implant.

In an aspect, a disclosed container can be a syringe. In an aspect, a syringe can be a glass syringe or a non-glass syringe. In an aspect, a syringe can comprise a perforated barrel. In an aspect, a syringe can comprise a distal end having no seal. In an aspect, a distal end having no seal can facilitate desiccation. In an aspect, a distal end having no seal can facilitate the extrusion or expelling of the composition. In an aspect, a disclosed container can be a glass container or a non-glass container. In an aspect, a disclosed container can be a glass vial or a non-glass vial. In an aspect, a disclosed container can comprise a stopper or a seal. In an aspect, a stopper or seal can comprise siliconized or non-siliconized rubber. In an aspect, a stopper or seal can comprise metal. In an aspect, the stopper or seal can comprise metal. In an aspect, a stopper or seal can comprise a Teflon coating or a Teflon treatment.

In an aspect, the composition contained within a disclosed container can be desiccated. In an aspect, the composition contained within a disclosed container hardens upon desiccation into a bioactive implant. In an aspect, the hardened bioactive implant has a predetermined size and shape.

In an aspect, the bioactive implant can be osteogenic. In an aspect, the bioactive implant can be chondrogenic. In an aspect, the bioactive implant can have one or more smooth and even surfaces. In an aspect, the bioactive implant can have one or more rough and uneven surfaces. In an aspect, the rough and uneven surface can be pitted. In an aspect, the rough and uneven surfaces can facilitate vascular ingrowth.

In an aspect, a composition comprising bone microparticles can be used in a spinal fusion, to treat or repair a maxillary defect, a mandibular defect, or both, to treat or repair a traumatic or a degenerative loss of bone, or both, to treat or repair a bone defect that follows a tumor resection, or a combination thereof. In an aspect, the bioactive implant can be used to treat or repair one or more of these bone defects or conditions.

In an aspect, a composition comprising cartilage microparticles can be to treat or repair a traumatic loss or a degenerative loss of cartilage, or both, to treat or repair a cartilage defect following a tumor resection, to treat or repair a degenerative chondrol lesion, a traumatic chondral lesion, or both, or a combination thereof. In an aspect, the bioactive implant can be used to treat or repair one or more of these cartilage defects or conditions.

In an aspect, the size of the bone microparticles in the composition contained within a disclosed container can range from about 20 µm to about 100 µm, from about 100 µm to about 200 µm, from about 200 µm to about 300 µm, from about 300 µm to about 400 µm, from about 400 µm to about 500 µm, from about 500 µm to about 600 µm, from about 600 µm to about 700 µm, or from about 700 µm to about 800 µm.

In an aspect, the size of the cartilage microparticles in the composition contained within a disclosed container can range from about 50 µm to about 100 µm, from about 100 µm to about 150 µm, from about 150 µm to about 200 µm, from about 200 µm to about 250 µm, from about 250 µm to about 300 µm, from about 300 µm to about 350 µm, from about 350 µm to about 400 µm, from about 400 µm to about 450 µm, from about 450 µm to about 500 µm, from about 500 µm to about 550 µm, from about 550 µm to about 600 µm, from about 600 µm to about 650 µm, from about 650 µm to about 700 µm, from about 700 µm to about 750 µm, from about 750 µm to about 800 µm, from about 800 µm to about 850 µm, or from about 850 µm to about 900 µm.

In an aspect, the bone microparticles in a disclosed composition contained within a disclosed container can be non-decalcified. In an aspect, the bone microparticles in a disclosed composition contained within a disclosed container can be decalcified. In an aspect, the bone microparticles in a disclosed composition contained within a disclosed container can comprise non-decalcified particles, decalcified particles, partially decalcified particles, demineralized bone matrix, or a combination thereof. In an aspect, a combination can comprise non-decalcified particles (NDP), decalcified particles (DP), partially decalcified particles (PDP), and demineralized bone matrix (DBM). In an aspect, a combination can comprise non-decalcified particles (NDP), decalcified particles (DP), and partially decalcified particles (PDP). In an aspect, a combination can comprise non-decalcified particles (NDP) and decalcified particles (DP). In an aspect, a combination can comprise non-decalcified particles (NDP) and partially decalcified particles (PDP). In an aspect, a combination can comprise non-decalcified particles (NDP) and demineralized bone matrix (DBM). In an aspect, a combination can comprise decalcified particles (DP) and partially decalcified particles (PDP). In an aspect, a combination can comprise decalcified particles (DP), partially decalcified particles (PDP), and demineralized bone matrix (DBM). In an aspect, a combination can comprise decalcified particles (DP) and demineralized bone matrix (DBM). In an aspect, a combination can comprise partially decalcified particles (PDP) and demineralized bone matrix (DBM). See, e.g., Table 1.

In an aspect, the amount of any one component (such as, for example, NDP, DP, PDP, or DMB) in a disclosed combination can range from about 1:1 to about 1:10 when compared to any other component. Alternatively, the amount of any one component (such as, for example, NDP, DP, PDP, or DMB) in a disclosed combination can range from about 1:10 to about 1:1 when compared to any other component. For example, the amount of one component (e.g., NDP microparticles) to a second component (e.g., DP microparticles) in a disclosed composition can be about 1:1, 1:2, 1:3, 1:4, 1:5, 1:6, 1:7, 1:8, 1:9, or 1:10, or 10:1, 9:1, 8:1, 7:1, 6:1, 5:1, 4:1, 3:1, or 2:1.

In an aspect, the cartilage microparticles in the composition contained within a disclosed container can be non-decalcified. In an aspect, the cartilage microparticles in the composition contained within a disclosed container can be decalcified.

In an aspect, the composition comprising bone microparticles contained within a disclosed container can comprise about 10% to about 70% w/v of bone microparticles, or about 10% to about 35% w/v of bone microparticles, or about 25% w/v of bone microparticles, or about 50% w/v of bone microparticles.

In an aspect, the composition a composition comprising cartilage microparticles contained within a disclosed container can comprise about 10% to about 70% w/v of cartilage microparticles, or about 10% to about 35% w/v of cartilage microparticles, or about 25% w/v of cartilage microparticles, or about 50% w/v of cartilage microparticles.

In an aspect, the bone microparticles or the cartilage microparticles can be obtained from an allogeneic source, a syngeneic source, or an autogeneic source. In an aspect, an allogeneic source can be a cadaver. In an aspect, the bone microparticles can be obtained from one or more sources (i.e., one or more donors). In an aspect, the cartilage microparticles can be obtained from one or more sources (i.e., one or more donors).

In an aspect, the solution of a composition contained with a disclosed container can comprise hydroxyethyl starch. In an aspect, the solution of a disclosed composition can comprise non-solubilized hydroxyethyl starch. In an aspect, the solution of a disclosed composition can comprise about 6% hydroxyethyl starch. In an aspect, a HES solution can be converted into a putty, a gel, or a paste. In an aspect, the HES solution can be converted into a putty, a gel, or a paste via evaporation, the introduction of additional bone microparticles, or the introduction of additional cartilage microparticles. In an aspect, the HES solution can be converted into a putty, a gel, or a paste via evaporation, the introduction of additional bone chips, shavings, or powder, or the introduction of additional cartilage chips, shavings, or powder. In an aspect, a disclosed HES solution is non-toxic. In an aspect, a disclosed HES solution comprises non-toxic components. In an aspect, a disclosed HES solution is safe for administration to human beings or other mammals.

In an aspect, the solution of a disclosed composition can comprise polyvinyl pyrrolidone (PVP). In an aspect, the PVP can comprise various molecular weights. In an aspect, the PVP can have an average molecular weight of 40,000. PVPs are known to the skilled person in the art. In an aspect, a PVP solution can be converted into a putty, a gel, or a paste. In an aspect, the PVP solution can be converted into a putty, a gel, or a paste via evaporation, the introduction of additional bone microparticles, or the introduction of additional cartilage microparticles. In an aspect, the PVP solution can be converted into a putty, a gel, or a paste via evaporation, the introduction of additional bone chips, shavings, or powder, or the introduction of additional cartilage chips, shavings, or powder. In an aspect, a disclosed PVP solution is non-toxic. In an aspect, a disclosed PVP solution comprises non-toxic components. In an aspect, a disclosed PVP solution is safe for administration to human beings or other mammals.

In an aspect, the solution of a disclosed composition can comprise povidone iodine. In an aspect, a povidone iodine solution can be converted into a putty, a gel, or a paste. In an aspect, the povidone iodine solution can be converted into a putty, a gel, or a paste via evaporation, the introduction of additional bone microparticles, or the introduction of additional cartilage microparticles. In an aspect, the povidone iodine solution can be converted into a putty, a gel, or a paste via evaporation, the introduction of additional bone chips, shavings, or powder, or the introduction of additional cartilage chips, shavings, or powder. In an aspect, a disclosed povidone iodine solution is non-toxic. In an aspect, a disclosed povidone iodine solution comprises non-toxic components. In an aspect, a disclosed povidone iodine solution is safe for administration to human beings or other mammals.

In an aspect, the solution of a disclosed composition can comprise collagen. In an aspect, collagen can be tendon collagen, bone collagen, or a combination thereof. In an aspect, a collagen solution can be converted into a putty, a gel, or a paste. In an aspect, the collagen solution can be converted into a putty, a gel, or a paste via evaporation, the introduction of additional bone microparticles, or the introduction of additional cartilage microparticles. In an aspect, the collagen solution can be converted into a putty, a gel, or a paste via evaporation, the introduction of additional bone chips, shavings, or powder, or the introduction of additional cartilage chips, shavings, or powder. In an aspect, a disclosed collagen solution is non-toxic. In an aspect, a disclosed collagen solution comprises non-toxic components. In an aspect, a disclosed collagen solution is safe for administration to human beings or other mammals.

In an aspect, the solution of a disclosed composition can comprise albumin. In an aspect, albumin can be human albumin, recombinant albumin, bovine albumin, non-bovine albumin, egg albumin, transgenic albumin, or a combination thereof. In an aspect, an albumin solution can be converted into a putty, a gel, or a paste. In an aspect, the albumin solution can be converted into a putty, a gel, or a paste via evaporation, the introduction of additional bone microparticles, or the introduction of additional cartilage microparticles. In an aspect, the albumin solution can be converted into a putty, a gel, or a paste via evaporation, the introduction of additional bone chips, shavings, or powder, or the introduction of additional cartilage chips, shavings, or powder. In an aspect, a disclosed albumin solution is non-toxic. In an aspect, a disclosed albumin solution comprises non-toxic components. In an aspect, a disclosed albumin solution is safe for administration to human beings or other mammals.

In an aspect, the solution of a disclosed composition can comprise albumin. In an aspect, a disclosed solution can comprise one or more of the following solutes: hydroxyethyl starch (HES), non-solubilized HES, polyvinyl pyrrolidone (PVP), povidone iodine, bone collagen, tendon collagen, and albumin (e.g., human albumin, recombinant albumin, bovine albumin, non-bovine albumin, egg albumin, transgenic albumin). In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed solution can comprise one or more of the following solutes: hydroxyethyl starch (HES), non-solubilized HES, polyvinyl pyrrolidone (PVP), povidone iodine, bone collagen, and tendon collagen, but not albumin. In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, the composition contained within a disclosed container can comprise one or more agents. In an aspect, the agents can comprise therapeutic agents, bone morphogenetic proteins, anti-infective agents (e.g., anti-microbial agents, anti-fungal agents, and combinations thereof), growth factors, growth hormones, antibiotics, antioxidants, analgesics, vitamins (e.g., vitamin D, vitamin K, and combinations thereof), sterilizing agents (e.g., iodine, bromine, calcium salts, and combinations thereof).

In an aspect, the solvent of the solution contained within a disclosed container can comprise water. In an aspect, the solvent of the solution contained within a disclosed container can comprise saline. In an aspect, the solvent of the solution contained within a disclosed container can comprise DMSO. In an aspect, the solvent of the solution contained within a disclosed container can comprise a balanced salt solution. In an aspect, a balanced salt solution includes, but is not limited to, Hank's Balanced Salt Solution (HBSS), Earle's Balanced Salt Solution (EBSS), Phosphate-Buffered Saline (PBS), Dulbecco's Phosphate-Buffered Saline (DPBS), and combinations thereof.

In an aspect, the bone microparticles can be embedded evenly or embedded unevenly in the desiccated composition. In an aspect, the desiccated composition can comprise both evenly and unevenly embedded bone microparticles.

In an aspect, the cartilage microparticles can be embedded evenly or embedded unevenly in the desiccated composition. In an aspect, the desiccated composition can comprise both evenly and unevenly embedded cartilage microparticles.

Disclosed herein is a container comprising a composition comprising bone microparticles in a hydroxyethyl starch solution, wherein the size of the bone microparticles is from about 20 μm to about 800 μm, wherein the composition hardens upon desiccation into a bioactive implant.

Disclosed herein is a container comprising a composition comprising cartilage microparticles in a hydroxyethyl starch solution, wherein the size of the cartilage microparticles is from about 50 μm to about 900 μm, wherein the composition hardens upon desiccation into a bioactive implant. In an aspect, the hardened bioactive implant has a predetermined size and shape.

Disclosed herein is a container comprising a composition comprising bone microparticles in a polyvinyl pyrrolidone (PVP) solution, wherein the size of the bone microparticles is from about 20 μm to about 800 μm, wherein the composition hardens upon desiccation into a bioactive implant. In an aspect, the hardened bioactive implant has a predetermined size and shape.

Disclosed herein is a container comprising a composition comprising cartilage microparticles in a polyvinyl pyrrolidone (PVP) solution, wherein the size of the cartilage microparticles is from about 50 μm to about 900 μm, wherein the composition hardens upon desiccation into a bioactive implant. In an aspect, the hardened bioactive implant has a predetermined size and shape.

Disclosed herein is a container comprising a composition comprising bone microparticles in a povidone iodine solution, wherein the size of the bone microparticles is from about 20 μm to about 800 μm, wherein the composition hardens upon desiccation into a bioactive implant. In an aspect, the hardened bioactive implant has a predetermined size and shape.

Disclosed herein is a container comprising a composition comprising cartilage microparticles in a povidone iodine solution, wherein the size of the cartilage microparticles is from about 50 μm to about 900 μm, wherein the composition hardens upon desiccation into a bioactive implant. In an aspect, the hardened bioactive implant has a predetermined size and shape.

Disclosed herein is container comprising a composition comprising bone microparticles in a collagen solution, wherein the size of the bone microparticles is from about 20 μm to about 800 μm, wherein the composition hardens upon desiccation into a bioactive implant. In an aspect, the hardened bioactive implant has a predetermined size and shape.

Disclosed herein is container comprising a composition comprising cartilage microparticles in a collagen solution, wherein the size of the cartilage microparticles is from about 50 μm to about 900 μm, wherein the composition hardens upon desiccation into a bioactive implant. In an aspect, the hardened bioactive implant has a predetermined size and shape.

Disclosed herein is a container comprising a composition comprising bone microparticles in an albumin solution, wherein the size of the bone microparticles is from about 20 µm to about 800 µm, wherein the composition hardens upon desiccation into a bioactive implant. In an aspect, the hardened bioactive implant has a predetermined size and shape.

Disclosed herein is a container comprising a composition comprising cartilage microparticles in an albumin solution, wherein the size of the cartilage microparticles is from about 50 µm to about 900 µm, wherein the composition hardens upon desiccation into a bioactive implant. In an aspect, the hardened bioactive implant has a predetermined size and shape.

6. Kits

Disclosed herein is a kit comprising a container disclosed herein.

Disclosed herein is a kit comprising a container disclosed herein, wherein the container comprises a composition disclosed herein.

Disclosed herein is a kit comprising a container, wherein the container comprises a composition comprising bone microparticles in a solution.

Disclosed herein is a kit comprising a container, wherein the container comprises a composition comprising cartilage microparticles in a solution.

Disclosed herein is a kit comprising (i) bone microparticles, and (ii) instructions for preparing a composition comprising bone microparticles in a solution.

Disclosed herein is a kit comprising (i) cartilage microparticles, and (ii) instructions for preparing a composition comprising cartilage microparticles in a solution.

Disclosed herein is a kit comprising a container comprising a composition comprising bone microparticles in a solution, wherein the size of the bone microparticles is from about 20 µm to about 800 µm.

Disclosed herein is a kit comprising a container comprising a composition comprising cartilage microparticles in a solution, wherein the size of the cartilage microparticles is from about 50 µm to about 900 µm.

In an aspect, a disclosed kit can comprise instructions for using the composition.

In an aspect, the composition of a disclosed kit can be desiccated. In an aspect, the composition of a disclosed kit hardens upon desiccation into a bioactive implant. In an aspect, the hardened bioactive implant has a predetermined size and shape.

In an aspect, the bioactive implant can be osteogenic. In an aspect, the bioactive implant can have one or more smooth and even surfaces. In an aspect, the bioactive implant can have one or more rough and uneven surfaces. In an aspect, the rough and uneven surface can be pitted. In an aspect, the rough and uneven surfaces can facilitate vascular ingrowth.

In an aspect, the solution of the composition of a disclosed kit can be used in a spinal fusion, to treat or repair a maxillary defect, a mandibular defect, or both, to treat or repair a traumatic or a degenerative loss of bone, or both, to treat or repair a bone defect that follows a tumor resection, or a combination thereof. In an aspect, the bioactive implant can be used to treat or repair one or more of these bone defects or conditions.

The bioactive implant can be to treat or repair a traumatic loss or a degenerative loss of cartilage, or both, to treat or repair a cartilage defect following a tumor resection, to treat or repair a degenerative chondrol lesion, a traumatic chondral lesion, or both, or a combination thereof.

In an aspect, the bioactive implant can be used to treat or repair one or more of these cartilage defects or conditions.

In an aspect, the solution of a composition contained with a disclosed container can comprise hydroxyethyl starch. In an aspect, the solution of a disclosed composition can comprise non-solubilized hydroxyethyl starch. In an aspect, the solution of a disclosed composition can comprise about 6% hydroxyethyl starch. In an aspect, a HES solution can be converted into a putty, a gel, or a paste. In an aspect, the HES solution can be converted into a putty, a gel, or a paste via evaporation, the introduction of additional bone microparticles, or the introduction of additional cartilage microparticles. In an aspect, the HES solution can be converted into a putty, a gel, or a paste via evaporation, the introduction of additional bone chips, shavings, or powder, or the introduction of additional cartilage chips, shavings, or powder. In an aspect, a disclosed HES solution is non-toxic. In an aspect, a disclosed HES solution comprises non-toxic components. In an aspect, a disclosed HES solution is safe for administration to human beings or other mammals.

In an aspect, the solution of a disclosed composition can comprise polyvinyl pyrrolidone (PVP). In an aspect, the PVP can comprise various molecular weights. In an aspect, the PVP can have an average molecular weight of 40,000. PVPs are known to the skilled person in the art. In an aspect, a PVP solution can be converted into a putty, a gel, or a paste. In an aspect, the PVP solution can be converted into a putty, a gel, or a paste via evaporation, the introduction of additional bone microparticles, or the introduction of additional cartilage microparticles. In an aspect, the PVP solution can be converted into a putty, a gel, or a paste via evaporation, the introduction of additional bone chips, shavings, or powder, or the introduction of additional cartilage chips, shavings, or powder. In an aspect, a disclosed PVP solution is non-toxic. In an aspect, a disclosed PVP solution comprises non-toxic components. In an aspect, a disclosed PVP solution is safe for administration to human beings or other mammals.

In an aspect, the solution of a disclosed composition can comprise povidone iodine. In an aspect, a povidone iodine solution can be converted into a putty, a gel, or a paste. In an aspect, the povidone iodine solution can be converted into a putty, a gel, or a paste via evaporation, the introduction of additional bone microparticles, or the introduction of additional cartilage microparticles. In an aspect, the povidone iodine solution can be converted into a putty, a gel, or a paste via evaporation, the introduction of additional bone chips, shavings, or powder, or the introduction of additional cartilage chips, shavings, or powder. In an aspect, a disclosed povidone iodine solution is non-toxic. In an aspect, a disclosed povidone iodine solution comprises non-toxic components. In an aspect, a disclosed povidone iodine solution is safe for administration to human beings or other mammals.

In an aspect, the solution of a disclosed composition can comprise collagen. In an aspect, collagen can be tendon collagen, bone collagen, or a combination thereof. In an aspect, a collagen solution can be converted into a putty, a gel, or a paste. In an aspect, the collagen solution can be converted into a putty, a gel, or a paste via evaporation, the introduction of additional bone microparticles, or the introduction of additional cartilage microparticles. In an aspect, the collagen solution can be converted into a putty, a gel, or a paste via evaporation, the introduction of additional bone chips, shavings, or powder, or the introduction of additional cartilage chips, shavings, or powder. In an aspect, a disclosed collagen solution is non-toxic. In an aspect, a disclosed collagen solution comprises non-toxic components. In an aspect, a disclosed collagen solution is safe for administration to human beings or other mammals.

In an aspect, the solution of a disclosed composition can comprise albumin. In an aspect, albumin can be human albumin, recombinant albumin, bovine albumin, non-bovine albumin, egg albumin, transgenic albumin, or a combination thereof. In an aspect, an albumin solution can be converted into a putty, a gel, or a paste. In an aspect, the albumin solution can be converted into a putty, a gel, or a paste via evaporation, the introduction of additional bone microparticles, or the introduction of additional cartilage microparticles. In an aspect, the albumin solution can be converted into a putty, a gel, or a paste via evaporation, the introduction of additional bone chips, shavings, or powder, or the introduction of additional cartilage chips, shavings, or powder. In an aspect, a disclosed albumin solution is non-toxic. In an aspect, a disclosed albumin solution comprises non-toxic components. In an aspect, a disclosed albumin solution is safe for administration to human beings or other mammals.

In an aspect, the solution of a disclosed composition can comprise albumin. In an aspect, a disclosed solution can comprise one or more of the following solutes: hydroxyethyl starch (HES), non-solubilized HES, polyvinyl pyrrolidone (PVP), povidone iodine, bone collagen, tendon collagen, and albumin (e.g., human albumin, recombinant albumin, bovine albumin, non-bovine albumin, egg albumin, transgenic albumin). In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed solution can comprise one or more of the following solutes: hydroxyethyl starch (HES), non-solubilized HES, polyvinyl pyrrolidone (PVP), povidone iodine, bone collagen, and tendon collagen, but not albumin. In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed kit can comprise at least one mold having a predetermined size and a predetermined shape. In an aspect, a mold can have a volume from about 1 mL to about 120 mL. In an aspect, a mold can have a volume from about 500 mL to about 2000 mL. In an aspect, a mold can have a volume greater than 2000 mL. In an aspect, a mold can be customized for a specific bone defect or bone defects of the subject. In an aspect, a mold can be customized for a specific cartilage defect or cartilage defects of the subject.

In an aspect, the size of the bone microparticles in a disclosed composition can range from about 20 µm to about 100 µm, from about 100 µm to about 200 µm, from about 200 µm to about 300 µm, from about 300 µm to about 400 µm, from about 400 µm to about 500 µm, from about 500 µm to about 600 µm, from about 600 µm to about 700 µm, or from about 700 µm to about 800 µm.

In an aspect, the composition of a disclosed kit can comprise about 10% to about 70% w/v of bone microparticles, or about 10% to about 35% w/v of bone microparticles, or about 25% w/v of bone microparticles, or about 50% w/v of bone microparticles.

In an aspect, the bone microparticles in the composition of a disclosed kit can be non-decalcified. In an aspect, the bone microparticles in the composition of a disclosed kit can be decalcified. In an aspect, the bone microparticles in the composition of a disclosed kit can comprise non-decalcified particles, decalcified particles, partially decalcified particles, demineralized bone matrix, or a combination thereof. In an aspect, a combination can comprise non-decalcified particles (NDP), decalcified particles (DP), partially decalcified particles (PDP), and demineralized bone matrix (DBM). In an aspect, a combination can comprise non-decalcified particles (NDP), decalcified particles (DP), and partially decalcified particles (PDP).

In an aspect, a combination can comprise non-decalcified particles (NDP) and decalcified particles (DP). In an aspect, a combination can comprise non-decalcified particles (NDP) and partially decalcified particles (PDP). In an aspect, a combination can comprise non-decalcified particles (NDP) and demineralized bone matrix (DBM). In an aspect, a combination can comprise decalcified particles (DP) and partially decalcified particles (PDP). In an aspect, a combination can comprise decalcified particles (DP), partially decalcified particles (PDP), and demineralized bone matrix (DBM). In an aspect, a combination can comprise decalcified particles (DP) and demineralized bone matrix (DBM). In an aspect, a combination can comprise partially decalcified particles (PDP) and demineralized bone matrix (DBM). See, e.g., Table 1.

In an aspect, the amount of any one component (such as, for example, NDP, DP, PDP, or DMB) in a disclosed combination can range from about 1:1 to about 1:10 when compared to any other component. Alternatively, the amount of any one component (such as, for example, NDP, DP, PDP, or DMB) in a disclosed combination can range from about 1:10 to about 1:1 when compared to any other component. For example, the amount of one component (e.g., NDP microparticles) to a second component (e.g., DP microparticles) in a disclosed composition can be about 1:1, 1:2, 1:3, 1:4, 1:5, 1:6, 1:7, 1:8, 1:9, or 1:10, or 10:1, 9:1, 8:1, 7:1, 6:1, 5:1, 4:1, 3:1, or 2:1.

In an aspect, the size of the cartilage microparticles can range from about 50 µm to about 100 µm, from about 100 µm to about 150 µm, from about 150 µm to about 200 µm, from about 200 µm to about 250 µm, from about 250 µm to about 300 µm, from about 300 µm to about 350 µm, from about 350 µm to about 400 µm, from about 400 µm to about 450 µm, from about 450 µm to about 500 µm, from about 500 µm to about 550 µm, from about 550 µm to about 600 µm, from about 600 µm to about 650 µm, from about 650 µm to about 700 µm, from about 700 µm to about 750 µm, from about 750 µm to about 800 µm, from about 800 µm to about 850 µm, or from about 850 µm to about 900 µm.

In an aspect, the composition of a disclosed kit can comprise about 10% to about 70% w/v of cartilage microparticles, or about 10% to about 35% w/v of cartilage microparticles, or about 25% w/v of cartilage microparticles, or about 50% w/v of cartilage microparticles.

In an aspect, the cartilage microparticles in the composition of a disclosed kit can be non-decalcified. In an aspect, the cartilage microparticles in the composition of a disclosed kit can be decalcified.

In an aspect, the bone microparticles or the cartilage microparticles in a disclosed kit can be obtained from an allogeneic source, a syngeneic source, or an autogeneic source. In an aspect, an allogeneic source can be a cadaver. In an aspect, the bone microparticles can be obtained from one or more sources (i.e., one or more donors). In an aspect, the cartilage microparticles can be obtained from one or more sources (i.e., one or more donors).

In an aspect, the solvent of the solution of a disclosed kit can comprise water. In an aspect, the solvent of the solution of a disclosed kit can comprise saline. In an aspect, the solvent of the solution of a disclosed kit can comprise DMSO. In an aspect, the solvent of the solution of a disclosed kit can comprise alcohol. In an aspect, the solvent of the solution of a disclosed kit can comprise a balanced salt solution. In an aspect, a balanced salt solution includes, but is not limited to, Hank's Balanced Salt Solution (HBSS), Earle's Balanced Salt Solution (EBSS), Phosphate-Buffered Saline (PBS), Dulbecco's Phosphate-Buffered Saline (DPBS), and combinations thereof.

In an aspect, a disclosed kit can comprise one or more agents. In an aspect, the one or more agents can be added to a solution. In an aspect, the agents can comprise therapeutic agents, bone morphogenetic proteins, anti-infective agents (e.g., anti-microbial agents, anti-fungal agents, and combinations thereof), growth factors, growth hormones, antibiotics, antioxidants, analgesics, vitamins (e.g., vitamin D, vitamin K, and combinations thereof), sterilizing agents (e.g., iodine, bromine, calcium salts, and combinations thereof).

In an aspect, the bone microparticles can be embedded evenly or embedded unevenly in the desiccated composition. In an aspect, the cartilage microparticles can be embedded evenly or embedded unevenly in the desiccated composition. In an aspect, the desiccated composition can comprise both evenly and unevenly embedded bone microparticles. In an aspect, the desiccated composition can comprise both evenly and unevenly embedded cartilage microparticles.

Disclosed herein is a kit comprising (i) bone microparticles, (ii) hydroxyethyl starch, and (iii) instructions for preparing a composition comprising bone microparticles in a hydroxyethyl starch solution.

Disclosed herein is a kit comprising (i) bone microparticles, (ii) hydroxyethyl starch, (iii) at least one mold of a pre-determined size and shape, (iv) instructions for preparing a composition comprising bone microparticles in a hydroxyethyl starch solution, and (v) instructions for using the composition.

Disclosed herein is a kit comprising (i) bone microparticles, (ii) at least one mold of a pre-determined size and shape, (iii) instructions for preparing a composition comprising bone microparticles in a hydroxyethyl starch solution, and (iv) instructions for using the composition.

Disclosed herein is a kit comprising (i) cartilage microparticles, (ii) hydroxyethyl starch, and (iii) instructions for preparing a composition comprising cartilage microparticles in a hydroxyethyl starch solution.

Disclosed herein is a kit comprising (i) cartilage microparticles, (ii) hydroxyethyl starch, (iii) at least one mold of a pre-determined size and shape, (iv) instructions for preparing a composition comprising cartilage microparticles in a hydroxyethyl starch solution, and (v) instructions for using the composition.

Disclosed herein is a kit comprising (i) cartilage microparticles, (ii) at least one mold of a pre-determined size and shape, (iii) instructions for preparing a composition comprising cartilage microparticles in a hydroxyethyl starch solution, and (iv) instructions for using the composition.

C. Methods

1. Methods of Making a Bioactive Implant Comprising Bone Microparticles

Disclosed herein is a method of making a bioactive implant, the method comprising desiccating a composition disclosed herein.

Disclosed herein is a method of making a bioactive implant, the method comprising desiccating a composition comprising bone microparticles in a solution.

Disclosed herein is a method of making a bioactive implant, the method comprising desiccating a composition comprising bone microparticles in a solution, wherein the size of the bone microparticles is from about 20 µm to about 800 µm.

In an aspect, desiccating comprises producing a hardened bioactive implant having a predetermined size and shape.

In an aspect, a disclosed method can comprise preparing the composition.

In an aspect, preparing the composition can comprise adding bone microparticles to a solvent to generate a solution.

In an aspect, the solvent can comprise water. In an aspect, the solvent can comprise saline. In an aspect, the solvent can comprise DMSO. In an aspect, the solvent can comprise alcohol. In an aspect, the solvent can comprise a balanced salt solution. In an aspect, a balanced salt solution includes, but is not limited to, Hank's Balanced Salt Solution (HBSS), Earle's Balanced Salt Solution (EBSS), Phosphate-Buffered Saline (PBS), Dulbecco's Phosphate-Buffered Saline (DPBS), and combinations thereof.

In an aspect, the solution of a disclosed composition can comprise hydroxyethyl starch. In an aspect, the solution of a disclosed composition can comprise non-solubilized hydroxyethyl starch. In an aspect, the solution of a disclosed composition can comprise about 6% hydroxyethyl starch. In an aspect, a HES solution can be converted into a putty, a gel, or a paste. In an aspect, the HES solution can be converted into a putty, a gel, or a paste via evaporation or the introduction of additional bone microparticles. In an aspect, the HES solution can be converted into a putty, a gel, or a paste via evaporation or the introduction of additional bone chips, shavings, or powder. In an aspect, a disclosed HES solution is non-toxic. In an aspect, a disclosed HES solution comprises non-toxic components. In an aspect, a disclosed HES solution is safe for administration to human beings or other mammals.

In an aspect, the solution of a disclosed composition can comprise polyvinyl pyrrolidone (PVP). In an aspect, the PVP can comprise various molecular weights. In an aspect, the PVP can have an average molecular weight of 40,000. PVPs are known to the skilled person in the art. In an aspect, a PVP solution can be converted into a putty, a gel, or a paste. In an aspect, the PVP solution can be converted into a putty, a gel, or a paste via evaporation or the introduction of additional bone microparticles. In an aspect, the PVP solution can be converted into a putty, a gel, or a paste via evaporation or the introduction of additional bone chips, shavings, or powder. In an aspect, a disclosed PVP solution is non-toxic. In an aspect, a disclosed PVP solution comprises non-toxic components. In an aspect, a disclosed PVP solution is safe for administration to human beings or other mammals.

In an aspect, the solution of a disclosed composition can comprise povidone iodine. In an aspect, a povidone iodine solution can be converted into a putty, a gel, or a paste. In an aspect, the povidone iodine solution can be converted into a putty, a gel, or a paste via evaporation or the introduction of additional bone microparticles. In an aspect, the povidone iodine solution can be converted into a putty, a gel, or a paste via evaporation or the introduction of additional bone chips, shavings, or powder. In an aspect, a disclosed povidone iodine solution is non-toxic. In an aspect, a disclosed povidone iodine solution comprises non-toxic components. In an aspect, a disclosed povidone iodine solution is safe for administration to human beings or other mammals.

In an aspect, the solution of a disclosed composition can comprise collagen. In an aspect, collagen can be tendon collagen, bone collagen, or a combination thereof. In an aspect, a collagen solution can be converted into a putty, a gel, or a paste. In an aspect, the collagen solution can be converted into a putty, a gel, or a paste via evaporation or the introduction of additional bone microparticles. In an aspect, the collagen solution can be converted into a putty, a gel, or a paste via evaporation or the introduction of additional bone chips, shavings, or powder. In an aspect, a disclosed collagen solution is non-toxic. In an aspect, a disclosed collagen solution comprises non-toxic components. In an aspect, a disclosed collagen solution is safe for administration to human beings or other mammals.

In an aspect, the solution of a disclosed composition can comprise albumin. In an aspect, albumin can be human albumin, recombinant albumin, bovine albumin, non-bovine albumin, egg albumin, transgenic albumin, or a combination thereof. In an aspect, an albumin solution can be converted into a putty, a gel, or a paste. In an aspect, the albumin solution can be converted into a putty, a gel, or a paste via evaporation or the introduction of additional bone microparticles. In an aspect, the albumin solution can be converted into a putty, a gel, or a paste via evaporation or the introduction of additional bone chips, shavings, or powder. In an aspect, a disclosed albumin solution is non-toxic. In an aspect, a disclosed albumin solution comprises non-toxic components. In an aspect, a disclosed albumin solution is safe for administration to human beings or other mammals.

In an aspect, a disclosed solution can comprise one or more of the following solutes: hydroxyethyl starch (HES), non-solubilized HES, polyvinyl pyrrolidone (PVP), povidone iodine, bone collagen, tendon collagen, and albumin (e.g., human albumin, recombinant albumin, bovine albumin, non-bovine albumin, egg albumin, transgenic albumin). In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed solution can comprise one or more of the following solutes: hydroxyethyl starch (HES), non-solubilized HES, polyvinyl pyrrolidone (PVP), povidone iodine, bone collagen, and tendon collagen, but not albumin. In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, preparing the composition can comprise adding to the solution one or more agents. In an aspect, the agents can comprise therapeutic agents, bone morphogenetic proteins, anti-infective agents (e.g., anti-microbial agents, anti-fungal agents, and combinations thereof), growth factors, growth hormones, antibiotics, antioxidants, analgesics, vitamins (e.g., vitamin D, vitamin K, and combinations thereof), sterilizing agents (e.g., iodine, bromine, calcium salts, and combinations thereof).

In an aspect, the method can comprise adding to a mold the composition.

In an aspect, the at least one mold can have a volume from about 1 mL to about 120 mL. In an aspect, the at least one mold can have a volume from about 500 mL to about 2000 mL. In an aspect, the at least one mold can have a volume greater than 2000 mL. In an aspect, a mold can be customized for a specific bone defect or bone defects of the subject.

In an aspect, the size of the bone microparticles in a disclosed composition can range from about 20 μm to about 100 μm, from about 100 μm to about 200 μm, from about 200 μm to about 300 μm, from about 300 μm to about 400 μm, from about 400 μm to about 500 μm, from about 500 μm to about 600 μm, from about 600 μm to about 700 μm, or from about 700 μm to about 800 μm.

In an aspect, the disclosed composition can comprise about 10% to about 70% w/v of bone microparticles, or about 10% to about 35% w/v of bone microparticles, or about 25% w/v of bone microparticles, or about 50% w/v of bone microparticles.

In an aspect, the bone microparticles can be non-decalcified. In an aspect, the bone microparticles can be decalcified. In an aspect, the bone microparticles can comprise non-decalcified particles, decalcified particles, partially decalcified particles, demineralized bone matrix, or a combination thereof. In an aspect, a combination can comprise non-decalcified particles (NDP), decalcified particles (DP), partially decalcified particles (PDP), and demineralized bone matrix (DBM). In an aspect, a combination can comprise non-decalcified particles (NDP), decalcified particles (DP), and partially decalcified particles (PDP). In an aspect, a combination can comprise non-decalcified particles (NDP) and decalcified particles (DP). In an aspect, a combination can comprise non-decalcified particles (NDP) and partially decalcified particles (PDP). In an aspect, a combination can comprise non-decalcified particles (NDP) and demineralized bone matrix (DBM). In an aspect, a combination can comprise decalcified particles (DP) and partially decalcified particles (PDP). In an aspect, a combination can comprise decalcified particles (DP), partially decalcified particles (PDP), and demineralized bone matrix (DBM). In an aspect, a combination can comprise decalcified particles (DP) and demineralized bone matrix (DBM). In an aspect, a combination can comprise partially decalcified particles (PDP) and demineralized bone matrix (DBM). See, e.g., Table 1.

In an aspect, the amount of any one component (such as, for example, NDP, DP, PDP, or DMB) in a disclosed combination can range from about 1:1 to about 1:10 when compared to any other component. Alternatively, the amount of any one component (such as, for example, NDP, DP, PDP, or DMB) in a disclosed combination can range from about 1:10 to about 1:1 when compared to any other component. For example, the amount of one component (e.g., NDP microparticles) to a second component (e.g., DP microparticles) in a disclosed composition can be about 1:1, 1:2, 1:3, 1:4, 1:5, 1:6, 1:7, 1:8, 1:9, or 1:10, or 10:1, 9:1, 8:1, 7:1, 6:1, 5:1, 4:1, 3:1, or 2:1.

In an aspect, desiccating the composition can occur in a vacuum. In an aspect, the vacuum can measure at about 400 millitorr or less. In an aspect, the vacuum can measure at about 300 millitorr or less. In an aspect, the vacuum can measure at about 200 millitorr or less. In an aspect, the vacuum can measure at about 100 millitorr or less.

In an aspect, desiccating the composition can comprise freeze-drying the composition. In an aspect, freeze-drying can comprise an amount of time from about 24 hours to about 120 hours. For example, in an aspect, freeze-drying can comprise 24 hours, 48 hours, 72 hours, 96 hours, or 120 hours, or some amount of time between 24 and 48 hours, between 48 and 72 hours, between 72 and 96 hours, or between 96 and 120 hours.

In an aspect, freeze-drying can occur at a temperature from about −40° C. to about −80° C. For example, in an aspect, freeze-drying can occur at −40° C., −50° C., −60° C., −70° C., or −80° C., or at some temperature between −40° C. and −50° C., −50° C. and −60° C., −60° C. and −70° C., or −70° C. and −80° C.

In an aspect, desiccating the composition can comprise subjecting the composition to hypothermic dehydration. In an aspect, hypothermic dehydration can occur at a temperature from about 2° C. to about 10° C. In an aspect, for example, hypothermic dehydration can occur at 2° C., 3° C., 4° C., 5° C., 6° C., 7° C., 8° C., 9° C., or 10° C., or at some temperature between 2° C. and 3° C., 3° C. and 4° C., 4° C. and 5° C., 5° C. and 6° C., 6° C. and 7° C., 7° C. and 8° C., 8° C. and 9° C., or 9° C. and 10° C. In an aspect, hypothermic dehydration can comprise an amount of time from about 24 to about 72 hours. For example, in an aspect, hypothermic dehydration can occur 24 hours, 48 hours, or 72 hours, or some amount of time between 24 and 48 hours or between 48 and 72 hours.

In an aspect, the bioactive implant can be osteogenic. In an aspect, the bioactive implant can have one or more smooth and even surfaces. In an aspect, the bioactive implant can have one or more rough and uneven surfaces. In an aspect, the rough and uneven surface can be pitted. In an aspect, the rough and uneven surfaces can facilitate vascular ingrowth.

In an aspect, the bioactive implant can be used in a spinal fusion, to treat or repair a maxillary defect, a mandibular defect, or both, to treat or repair a traumatic or a degenerative loss of bone, or both, to treat or repair a bone defect that follows a tumor resection, or a combination thereof. In an aspect, the bioactive implant can be used to treat or repair one or more of these defects or conditions.

In an aspect, one or more steps of a disclosed method can be modified, changed, repeated, or altered.

In an aspect, the bone microparticles can be embedded evenly or embedded unevenly in the desiccated composition. In an aspect, the desiccated composition can comprise both evenly and unevenly embedded bone microparticles.

Disclosed herein is a method of making a bioactive implant, the method comprising desiccating a composition comprising bone microparticles in a hydroxyethyl starch solution, wherein the size of the bone microparticles is from about 20 μm to about 800 μm. In an aspect, desiccating comprises producing a hardened bioactive implant having a predetermined size and shape.

Disclosed herein is a method of making a bioactive implant, the method comprising desiccating a composition comprising bone microparticles in a polyvinyl pyrrolidone (PVP) solution, wherein the size of the bone microparticles is from about 20 μm to about 800 μm. In an aspect, desiccating comprises producing a hardened bioactive implant having a predetermined size and shape.

Disclosed herein is a method of making a bioactive implant, the method comprising desiccating a composition comprising bone microparticles in a povidone iodine solution, wherein the size of the bone microparticles is from about 20 μm to about 800 μm. In an aspect, desiccating comprises producing a hardened bioactive implant having a predetermined size and shape.

Disclosed herein is a method of making a bioactive implant, the method comprising desiccating a composition comprising bone microparticles in a collagen solution, wherein the size of the bone microparticles is from about 20 μm to about 800 μm. In an aspect, desiccating comprises producing a hardened bioactive implant having a predetermined size and shape.

Disclosed herein is a method of making a bioactive implant, the method comprising desiccating a composition comprising bone microparticles in an albumin solution, wherein the size of the bone microparticles is from about 20 μm to about 800 μm. In an aspect, desiccating comprises producing a hardened bioactive implant having a predetermined size and shape.

Disclosed herein is a method of making a bioactive implant, the method comprising adding to a mold a disclosed composition; and desiccating the composition. In an aspect, desiccating comprises producing a hardened bioactive implant having a predetermined size and shape.

Disclosed herein is a method of making a bioactive implant, the method comprising adding to a mold a composition comprising bone microparticles in a solution; and desiccating the composition. In an aspect, desiccating comprises producing a hardened bioactive implant having a predetermined size and shape.

Disclosed herein is a method of making a bioactive implant, the method comprising preparing a composition comprising bone microparticles in a solution; adding to a mold the composition; and desiccating the composition. In an aspect, desiccating comprises producing a hardened bioactive implant having a predetermined size and shape.

Disclosed herein is a method of making a bioactive implant, the method comprising adding to a mold a composition comprising bone microparticles in a solution, wherein the size of the bone microparticles is from about 20 µm to about 800 µm; and desiccating the composition. In an aspect, desiccating comprises producing a hardened bioactive implant having a predetermined size and shape.

Disclosed herein is a method of making a bioactive implant, the method comprising preparing a composition comprising bone microparticles in a solution, wherein the size of the bone microparticles is from about 20 µm to about 800 µm; adding to a mold the composition; and desiccating the composition. In an aspect, desiccating comprises producing a hardened bioactive implant having a predetermined size and shape.

Disclosed herein is a method of making a bioactive implant with one or more smooth and even surfaces, the method comprising desiccating a composition disclosed herein. In an aspect, desiccating comprises producing a hardened bioactive implant having a predetermined size and shape.

Disclosed herein is a method of making a bioactive implant with one or more rough and uneven surfaces, the method comprising desiccating a composition disclosed herein. In an aspect, desiccating comprises producing a hardened bioactive implant having a predetermined size and shape.

Disclosed herein is a method of making a bioactive implant with one or more smooth and even surfaces, the method comprising desiccating a composition comprising bone microparticles in a solution, wherein the size of the bone microparticles is from about 20 µm to about 800 µm. In an aspect, desiccating comprises producing a hardened bioactive implant having a predetermined size and shape.

Disclosed herein is a method of making a bioactive implant with one or more rough and uneven surfaces, the method comprising desiccating a composition comprising bone microparticles in a solution, wherein the size of the bone microparticles is from about 20 µm to about 800 µm. In an aspect, desiccating comprises producing a hardened bioactive implant having a predetermined size and shape.

2. Methods of Making a Bioactive Implant Comprising Cartilage Microparticles

Disclosed herein is a method of making a bioactive implant, the method comprising desiccating a composition comprising cartilage microparticles in a solution.

Disclosed herein is a method of making a bioactive implant, the method comprising desiccating a composition comprising cartilage microparticles in a solution, wherein the size of the cartilage microparticles is from about 50 µm to about 900 µm.

In an aspect, desiccating comprises producing a hardened bioactive implant having a predetermined size and shape.

In an aspect, a disclosed method can comprise preparing the composition.

In an aspect, preparing the composition can comprise adding cartilage microparticles to a solvent to generate a solution.

In an aspect, the solvent can comprise water. In an aspect, the solvent can comprise saline. In an aspect, the solvent can comprise DMSO. In an aspect, the solvent can comprise alcohol. In an aspect, the solvent can comprise a balanced salt solution. In an aspect, a balanced salt solution includes, but is not limited to, Hank's Balanced Salt Solution (HBSS), Earle's Balanced Salt Solution (EBSS), Phosphate-Buffered Saline (PBS), Dulbecco's Phosphate-Buffered Saline (DPBS), and combinations thereof.

In an aspect, the solution of a disclosed composition can comprise hydroxyethyl starch. In an aspect, the solution of a disclosed composition can comprise non-solubilized hydroxyethyl starch. In an aspect, the solution of a disclosed composition can comprise about 6% hydroxyethyl starch. In an aspect, a HES solution can be converted into a putty, a gel, or a paste. In an aspect, the HES solution can be converted into a putty, a gel, or a paste via evaporation or the introduction of cartilage microparticles. In an aspect, the HES solution can be converted into a putty, a gel, or a paste via evaporation or the introduction of additional cartilage chips, shavings, or powder. In an aspect, a disclosed HES solution is non-toxic. In an aspect, a disclosed HES solution comprises non-toxic components. In an aspect, a disclosed HES solution is safe for administration to human beings or other mammals.

In an aspect, the solution of a disclosed composition can comprise polyvinyl pyrrolidone (PVP). In an aspect, the PVP can comprise various molecular weights. In an aspect, the PVP can have an average molecular weight of 40,000. PVPs are known to the skilled person in the art. In an aspect, a PVP solution can be converted into a putty, a gel, or a paste. In an aspect, the PVP solution can be converted into a putty, a gel, or a paste via evaporation or the introduction of additional cartilage microparticles. In an aspect, the PVP solution can be converted into a putty, a gel, or a paste via evaporation or the introduction of additional cartilage chips, shavings, or powder. In an aspect, a disclosed PVP solution is non-toxic. In an aspect, a disclosed PVP solution comprises non-toxic components. In an aspect, a disclosed PVP solution is safe for administration to human beings or other mammals.

In an aspect, the solution of a disclosed composition can comprise povidone iodine. In an aspect, a povidone iodine solution can be converted into a putty, a gel, or a paste. In an aspect, the povidone iodine solution can be converted into a putty, a gel, or a paste via evaporation or the introduction of additional cartilage microparticles. In an aspect, the povidone iodine solution can be converted into a putty, a gel, or a paste via evaporation or the introduction of additional cartilage chips, shavings, or powder. In an aspect, a disclosed povidone iodine solution is non-toxic. In an aspect, a disclosed povidone iodine solution comprises non-toxic components. In an aspect, a disclosed povidone iodine solution is safe for administration to human beings or other mammals.

In an aspect, the solution of a disclosed composition can comprise collagen. In an aspect, collagen can be tendon collagen, bone collagen, or a combination thereof. In an aspect, a collagen solution can be converted into a putty, a gel, or a paste. In an aspect, the collagen solution can be converted into a putty, a gel, or a paste via evaporation or the introduction of additional cartilage microparticles. In an aspect, the collagen solution can be converted into a putty, a gel, or a paste via evaporation or the introduction of additional cartilage chips, shavings, or powder. In an aspect, a disclosed collagen solution is non-toxic. In an aspect, a disclosed collagen solution comprises non-toxic components. In an aspect, a disclosed collagen solution is safe for administration to human beings or other mammals.

In an aspect, the solution of a disclosed composition can comprise albumin. In an aspect, albumin can be human albumin, recombinant albumin, bovine albumin, non-bovine albumin, egg albumin, transgenic albumin, or a combination thereof. In an aspect, an albumin solution can be converted into a putty, a gel, or a paste. In an aspect, the albumin solution can be converted into a putty, a gel, or a paste via evaporation or the introduction of additional cartilage microparticles. In an aspect, the albumin solution can be converted into a putty, a gel, or a paste via evaporation or the introduction of additional cartilage chips, shavings, or powder. In an aspect, a disclosed albumin solution is non-toxic. In an aspect, a disclosed albumin solution comprises non-toxic components. In an aspect, a disclosed albumin solution is safe for administration to human beings or other mammals.

In an aspect, a disclosed solution can comprise one or more of the following solutes: hydroxyethyl starch (HES), non-solubilized HES, polyvinyl pyrrolidone (PVP), povidone iodine, bone collagen, tendon collagen, and albumin (e.g., human albumin, recombinant albumin, bovine albumin, non-bovine albumin, egg albumin, transgenic albumin). In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed solution can comprise one or more of the following solutes: hydroxyethyl starch (HES), non-solubilized HES, polyvinyl pyrrolidone (PVP), povidone iodine, bone collagen, and tendon collagen, but not albumin. In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, preparing the composition can comprise adding to the solution one or more agents. In an aspect, the agents can comprise therapeutic agents, bone morphogenetic proteins, anti-infective agents (e.g., anti-microbial agents, anti-fungal agents, and combinations thereof), growth factors, growth hormones, antibiotics, antioxidants, analgesics, vitamins (e.g., vitamin D, vitamin K, and combinations thereof), sterilizing agents (e.g., iodine, bromine, calcium salts, and combinations thereof).

In an aspect, the method can comprise adding to a mold the composition.

In an aspect, the at least one mold can have a volume from about 1 mL to about 120 mL. In an aspect, the at least one mold can have a volume from about 500 mL to about 2000 mL. In an aspect, the at least one mold can have a volume greater than 2000 mL. In an aspect, a mold can be customized for a specific cartilage defect or cartilage defects of the subject.

In an aspect, the size of the cartilage microparticles can range from about 50 µm to about 100 µm, from about 100 µm to about 150 µm, from about 150 µm to about 200 µm, from about 200 µm to about 250 µm, from about 250 µm to about 300 µm, from about 300 µm to about 350 µm, from about 350 µm to about 400 µm, from about 400 µm to about 450 µm, from about 450 µm to about 500 µm, from about 500 µm to about 550 µm, from about 550 µm to about 600 µm, from about 600 µm to about 650 µm, from about 650 µm to about 700 µm, from about 700 µm to about 750 µm, from about 750 µm to about 800 µm, from about 800 µm to about 850 µm, or from about 850 µm to about 900 µm.

In an aspect, the disclosed composition can comprise about 10% to about 70% w/v of cartilage microparticles, or about 10% to about 35% w/v of cartilage microparticles, or about 25% w/v of cartilage microparticles, or about 50% w/v of cartilage microparticles.

In an aspect, the cartilage microparticles can be non-decalcified. In an aspect, the cartilage microparticles can be decalcified.

In an aspect, desiccating the composition can occur in a vacuum. In an aspect, the vacuum can measure at about 400 millitorr or less. In an aspect, the vacuum can measure at about 300 millitorr or less. In an aspect, the vacuum can measure at about 200 millitorr or less. In an aspect, the vacuum can measure at about 100 millitorr or less.

In an aspect, desiccating the composition can comprise freeze-drying the composition. In an aspect, freeze-drying can comprise an amount of time from about 24 hours to about 120 hours. For example, in an aspect, freeze-drying can comprise 24 hours, 48 hours, 72 hours, 96 hours, or 120 hours, or some amount of time between 24 and 48 hours, between 48 and 72 hours, between 72 and 96 hours, or between 96 and 120 hours.

In an aspect, freeze-drying can occur at a temperature from about −40° C. to about −80° C. For example, in an aspect, freeze-drying can occur at −40° C., −50° C., −60° C., −70° C., or −80° C., or at some temperature between −40° C. and −50° C., −50° C. and −60° C., −60° C. and −70° C., or −70° C. and −80° C.

In an aspect, desiccating the composition can comprise subjecting the composition to hypothermic dehydration. In an aspect, hypothermic dehydration can occur at a temperature from about 2° C. to about 10° C. In an aspect, for example, hypothermic dehydration can occur at 2° C., 3° C., 4° C., 5° C., 6° C., 7° C., 8° C., 9° C., or 10° C., or at some temperature between 2° C. and 3° C., 3° C. and 4° C., 4° C. and 5° C., 5° C. and 6° C., 6° C. and 7° C., 7° C. and 8° C., 8° C. and 9° C., or 9° C. and 10° C. In an aspect, hypothermic dehydration can comprise an amount of time from about 24 to about 72 hours. For example, in an aspect, hypothermic dehydration can occur 24 hours, 48 hours, or 72 hours, or some amount of time between 24 and 48 hours or between 48 and 72 hours.

In an aspect, the bioactive implant can be chondrogenic. In an aspect, the bioactive implant can have one or more smooth and even surfaces. In an aspect, the bioactive implant can have one or more rough and uneven surfaces. In an aspect, the rough and uneven surface can be pitted. In an aspect, the rough and uneven surfaces can facilitate vascular ingrowth.

In an aspect, the bioactive implant can be to treat or repair a traumatic loss or a degenerative loss of cartilage, or both, to treat or repair a cartilage defect following a tumor resection, to treat or repair a degenerative chondrol lesion, a traumatic chondral lesion, or both, or a combination thereof. In an aspect, the bioactive implant can be used to treat or repair one or more of these defects or conditions.

In an aspect, one or more steps of a disclosed method can be modified, changed, repeated, or altered.

In an aspect, the cartilage microparticles can be embedded evenly or embedded unevenly in the desiccated composition. In an aspect, the desiccated composition can comprise both evenly and unevenly embedded cartilage microparticles.

Disclosed herein is a method of making a bioactive implant, the method comprising desiccating a composition comprising cartilage microparticles in a hydroxyethyl starch solution, wherein the size of the cartilage microparticles is from about 50 µm to about 900 µm. In an aspect, desiccating comprises producing a hardened bioactive implant having a predetermined size and shape.

Disclosed herein is a method of making a bioactive implant, the method comprising desiccating a composition comprising cartilage microparticles in a polyvinyl pyrrolidone (PVP) solution, wherein the size of the cartilage microparticles is from about 50 µm to about 900 µm.

In an aspect, desiccating comprises producing a hardened bioactive implant having a predetermined size and shape.

Disclosed herein is a method of making a bioactive implant, the method comprising desiccating a composition comprising cartilage microparticles in a povidone iodine solution, wherein the size of the cartilage microparticles is from about 50 µm to about 900 µm. In an aspect, desiccating comprises producing a hardened bioactive implant having a predetermined size and shape.

Disclosed herein is a method of making a bioactive implant, the method comprising desiccating a composition comprising cartilage microparticles in a collagen solution, wherein the size of the cartilage microparticles is from about 50 µm to about 900 µm. In an aspect, desiccating comprises producing a hardened bioactive implant having a predetermined size and shape.

Disclosed herein is a method of making a bioactive implant, the method comprising desiccating a composition comprising cartilage microparticles in an albumin solution, wherein the size of the cartilage microparticles is from about 50 µm to about 900 µm. In an aspect, desiccating comprises producing a hardened bioactive implant having a predetermined size and shape.

Disclosed herein is a method of making a bioactive implant, the method comprising adding to a mold a disclosed composition; and desiccating the composition. In an aspect, desiccating comprises producing a hardened bioactive implant having a predetermined size and shape.

Disclosed herein is a method of making a bioactive implant, the method comprising adding to a mold a composition comprising cartilage microparticles in a solution; and desiccating the composition. In an aspect, desiccating comprises producing a hardened bioactive implant having a predetermined size and shape.

Disclosed herein is a method of making a bioactive implant, the method comprising preparing a composition comprising cartilage microparticles in a solution; adding to a mold the composition; and desiccating the composition. In an aspect, desiccating comprises producing a hardened bioactive implant having a predetermined size and shape.

Disclosed herein is a method of making a bioactive implant, the method comprising adding to a mold a composition comprising cartilage microparticles in a solution, wherein the size of the cartilage microparticles is from about 50 µm to about 900 µm; and desiccating the composition. In an aspect, desiccating comprises producing a hardened bioactive implant having a predetermined size and shape.

Disclosed herein is a method of making a bioactive implant, the method comprising preparing a composition comprising cartilage microparticles in a solution, wherein the size of the cartilage microparticles is from about 50 µm to about 900 µm; adding to a mold the composition; and desiccating the composition. In an aspect, desiccating comprises producing a hardened bioactive implant having a predetermined size and shape.

Disclosed herein is a method of making a bioactive implant with one or more smooth and even surfaces, the method comprising desiccating a composition disclosed herein. In an aspect, desiccating comprises producing a hardened bioactive implant having a predetermined size and shape.

Disclosed herein is a method of making a bioactive implant with one or more rough and uneven surfaces, the method comprising desiccating a composition disclosed herein. In an aspect, desiccating comprises producing a hardened bioactive implant having a predetermined size and shape.

Disclosed herein is a method of making a bioactive implant with one or more smooth and even surfaces, the method comprising desiccating a composition comprising cartilage microparticles in a solution, wherein the size of the cartilage microparticles is from about 50 µm to about 900 µm. In an aspect, desiccating comprises producing a hardened bioactive implant having a predetermined size and shape.

Disclosed herein is a method of making a bioactive implant with one or more rough and uneven surfaces, the method comprising desiccating a composition comprising cartilage microparticles in a solution, wherein the size of the cartilage microparticles is from about 50 µm to about 900 µm. In an aspect, desiccating comprises producing a hardened bioactive implant having a predetermined size and shape.

3. Methods of Treating or Repairing a Bone Defect

Disclosed herein is a method of treating or repairing a bone defect, the method comprising making a bioactive implant; and implanting the bioactive implant at the site of a bone defect.

Disclosed herein is a method of treating or repairing a bone defect, the method comprising implanting at the site of a bone defect a bioactive implant.

Disclosed herein is a method of treating or repairing a bone defect, the method comprising implanting at the site of a bone defect a bioactive implant made by a method disclosed herein.

Disclosed herein is a method of treating or repairing a bone defect, the method comprising: preparing a composition comprising bone microparticles in a solution, wherein the size of the bone microparticles is from about 20 µm to about 800 µm; adding the composition to a mold; desiccating the composition, thereby producing the bioactive implant; and implanting the bioactive implant at the site of a bone defect.

Disclosed herein is a method of treating or repairing a bone defect, the method comprising: preparing a composition comprising bone microparticles in a hydroxyethyl starch solution, wherein the size of the bone microparticles is from about 20 µm to about 800 µm; adding the composition to a mold; desiccating the composition, thereby producing the bioactive implant; and implanting the bioactive implant at the site of a bone defect.

In an aspect, desiccating comprises producing a hardened bioactive implant having a predetermined size and shape.

In an aspect, the bioactive implant can be used in a spinal fusion, to treat or repair a maxillary defect, a mandibular defect, or both, to treat or repair a traumatic or a degenerative loss of bone, or both, to treat or repair a bone defect that follows a tumor resection, or a combination thereof. In an aspect, the bioactive implant can be used to treat or repair one or more of these defects or conditions.

In an aspect, making the bioactive implant can comprise adding to a mold a composition comprising bone microparticles in a solution, wherein the size of the bone microparticles is from about 20 µm to about 800 µm, and desiccating the composition.

In an aspect, making the bioactive implant can comprise adding to a mold a composition comprising bone microparticles in a solution, and desiccating the composition.

In an aspect, a mold can have a predetermined size and a predetermined shape. In an aspect, a mold can have a volume from about 1 mL to about 120 mL. In an aspect, a mold can have a volume from about 500 mL to about 2000 mL. In an aspect, a mold can have a volume greater than 2000 mL. In an aspect, a mold can be customized for a specific bone defect or bone defects of the subject.

In an aspect, the size of the bone microparticles in a disclosed composition can range from about 20 µm to about 100 µm, from about 100 µm to about 200 µm, from about 200 µm to about 300 µm, from about 300 µm to about 400 µm, from about 400 µm to about 500 µm, from about 500 µm to about 600 µm, from about 600 µm to about 700 µm, or from about 700 µm to about 800 µm.

In an aspect, making the bioactive implant can comprise preparing a disclosed composition. In an aspect, preparing a disclosed composition can comprise adding bone microparticles to a solvent to generate a solution. In an aspect, the solvent can comprise water. In an aspect, the solvent can comprise saline. In an aspect, the solvent can comprise DMSO. In an aspect, the solvent can comprise alcohol. In an aspect, the solvent can comprise a balanced salt solution. In an aspect, a balanced salt solution includes, but is not limited to, Hank's Balanced Salt Solution (HBSS), Earle's Balanced Salt Solution (EBSS), Phosphate-Buffered Saline (PBS), Dulbecco's Phosphate-Buffered Saline (DPBS), and combinations thereof.

In an aspect, the solution of a disclosed composition can comprise hydroxyethyl starch. In an aspect, the solution of a disclosed composition can comprise non-solubilized hydroxyethyl starch. In an aspect, the solution of a disclosed composition can comprise about 6% hydroxyethyl starch. In an aspect, a HES solution can be converted into a putty, a gel, or a paste. In an aspect, the HES solution can be converted into a putty, a gel, or a paste via evaporation or the introduction of additional bone microparticles. In an aspect, the HES solution can be converted into a putty, a gel, or a paste via evaporation or the introduction of additional bone chips, shavings, or powder. In an aspect, a disclosed HES solution is non-toxic. In an aspect, a disclosed HES solution comprises non-toxic components. In an aspect, a disclosed HES solution is safe for administration to human beings or other mammals.

In an aspect, the solution of a disclosed composition can comprise polyvinyl pyrrolidone (PVP). In an aspect, the PVP can comprise various molecular weights. In an aspect, the PVP can have an average molecular weight of 40,000. PVPs are known to the skilled person in the art. In an aspect, a PVP solution can be converted into a putty, a gel, or a paste. In an aspect, the PVP solution can be converted into a putty, a gel, or a paste via evaporation or the introduction of additional bone microparticles. In an aspect, the PVP solution can be converted into a putty, a gel, or a paste via evaporation or the introduction of additional bone chips, shavings, or powder. In an aspect, a disclosed PVP solution is non-toxic. In an aspect, a disclosed PVP solution comprises non-toxic components. In an aspect, a disclosed PVP solution is safe for administration to human beings or other mammals.

In an aspect, the solution of a disclosed composition can comprise povidone iodine. In an aspect, a povidone iodine solution can be converted into a putty, a gel, or a paste. In an aspect, the povidone iodine solution can be converted into a putty, a gel, or a paste via evaporation or the introduction of additional bone microparticles. In an aspect, the povidone iodine solution can be converted into a putty, a gel, or a paste via evaporation or the introduction of additional bone chips, shavings, or powder. In an aspect, a disclosed povidone iodine solution is non-toxic. In an aspect, a disclosed povidone iodine solution comprises non-toxic components. In an aspect, a disclosed povidone iodine solution is safe for administration to human beings or other mammals.

In an aspect, the solution of a disclosed composition can comprise collagen. In an aspect, collagen can be tendon collagen, bone collagen, or a combination thereof. In an aspect, a collagen solution can be converted into a putty, a gel, or a paste. In an aspect, the collagen solution can be converted into a putty, a gel, or a paste via evaporation or the introduction of additional bone microparticles. In an aspect, the collagen solution can be converted into a putty, a gel, or a paste via evaporation or the introduction of additional bone chips, shavings, or powder. In an aspect, a disclosed collagen solution is non-toxic. In an aspect, a disclosed collagen solution comprises non-toxic components. In an aspect, a disclosed collagen solution is safe for administration to human beings or other mammals.

In an aspect, the solution of a disclosed composition can comprise albumin. In an aspect, albumin can be human albumin, recombinant albumin, bovine albumin, non-bovine albumin, egg albumin, transgenic albumin, or a combination thereof. In an aspect, an albumin solution can be converted into a putty, a gel, or a paste. In an aspect, the albumin solution can be converted into a putty, a gel, or a paste via evaporation or the introduction of additional bone microparticles. In an aspect, the albumin solution can be converted into a putty, a gel, or a paste via evaporation or the introduction of additional bone chips, shavings, or powder. In an aspect, a disclosed albumin solution is non-toxic. In an aspect, a disclosed albumin solution comprises non-toxic components. In an aspect, a disclosed albumin solution is safe for administration to human beings or other mammals.

In an aspect, a disclosed solution can comprise one or more of the following solutes: hydroxyethyl starch (HES), non-solubilized HES, polyvinyl pyrrolidone (PVP), povidone iodine, bone collagen, tendon collagen, and albumin (e.g., human albumin, recombinant albumin, bovine albumin, non-bovine albumin, egg albumin, transgenic albumin). In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed solution can comprise one or more of the following solutes: hydroxyethyl starch (HES), non-solubilized HES, polyvinyl pyrrolidone (PVP), povidone iodine, bone collagen, and tendon collagen, but not albumin. In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, preparing a disclosed composition can comprise adding to the solution one or more agents. In an aspect, the agents can comprise therapeutic agents, bone morphogenetic proteins, anti-infective agents (e.g., antimicrobial agents, anti-fungal agents, and combinations thereof), growth factors, growth hormones, antibiotics, antioxidants, analgesics, vitamins (e.g., vitamin D, vitamin K, and combinations thereof), sterilizing agents (e.g., iodine, bromine, calcium salts, and combinations thereof).

In an aspect, the disclosed composition can comprise about 10% to about 70% w/v of bone microparticles, or about 10% to about 35% w/v of bone microparticles, or about 25% w/v of bone microparticles, or about 50% w/v of bone microparticles.

In an aspect, making the bioactive implant can comprise adding to a mold a composition comprising bone microparticles in a hydroxyethyl starch solution, wherein the size of the bone microparticles is from about 20 μm to about 800 μm.

In an aspect, making the bioactive implant can comprise adding to a mold a composition comprising bone microparticles in a polyvinyl pyrrolidone (PVP) solution, wherein the size of the bone microparticles is from about 20 μm to about 800 μm; and desiccating the composition.

In an aspect, making the bioactive implant can comprise adding to a mold a composition comprising bone microparticles in a povidone iodine solution; and desiccating the composition.

In an aspect, making the bioactive implant can comprise adding to a mold a composition comprising bone microparticles in a collagen solution, wherein the size of the bone microparticles is from about 20 μm to about 800 μm; and desiccating the composition.

In an aspect, making the bioactive implant can comprise adding to a mold a composition comprising bone microparticles in an albumin solution, wherein the size of the bone microparticles is from about 20 μm to about 800 μm; and desiccating the composition.

In a disclosed method of treating or repairing a bone defect, the implanted bioactive implant can be replaced by the subject's bone.

In an aspect of a disclosed method, one or more bioactive implants can be implanted.

In an aspect of a disclosed method, a subject can receive one or more bioactive implants.

In an aspect, a disclosed method of treating or repairing a bone defect can comprise evaluating the effect of the implanted bioactive implant at one or more pre-determined times. In an aspect, the pre-determined times can comprise 1 to 7 days day post-implantation, or a time between 1 and 7 days post-implantation. In an aspect, the pre-determined times can comprise 1 to 4 weeks post-implantation, or a time between 1 and 4 weeks post-implantation. In an aspect, the pre-determined times can comprise 1 to 12 months post-implantation, or a time between 1 and 12 months post-implantation. In an aspect, the pre-determined times comprise 1 to 10 years post-implantation, or a time between 1 and 10 years post-implantation.

In an aspect, evaluating the effect of the implanted bioactive implant can comprise examining the incorporation of the bioactive implant. In an aspect, examining the incorporation of the bioactive implant can use one or more radiograph. Using one or more radiographs, the skilled person (e.g., a radiologist, an orthopedic surgeon, etc.) can determine (i) the presence or absence of trabeculae within the grafted defect, (ii) the overall bone density, (iii) the quality of bone at the border of graft (can be described as well defined, hazy, or invisible), (iv) the bone density within the defect (can be described as same as, equal to, or less than adjacent normal bone), or (v) a combination thereof.

In an aspect, a disclosed method of treating or repairing a bone defect can comprise evaluating the effect of the bioactive implant at one or more times post-implantation.

In an aspect, a disclosed method of treating or repairing a bone defect can comprise comprises systemically administering to the subject one or more agents. In an aspect, the one or more of agents can comprise therapeutic agents, bone morphogenetic proteins, anti-infective agents, growth factors, growth hormone, antibiotics, antioxidants, painkillers, vitamins, sterilizing agents, or a combination thereof. In an aspect, the one or more agents can be administered pre-implantation, during implantation, post-implantation, or a combination thereof. In an aspect, the one or more agents can be administered at one or more times. In an aspect, the one or more agents can be administered intravenously or orally.

In an aspect, one or more steps of a disclosed method can be modified, changed, repeated, or altered.

4. Methods of Treating or Repairing a Cartilage Defect

Disclosed herein is a method of treating or repairing a cartilage defect, the method comprising making a bioactive implant; and implanting the bioactive implant at the site of a cartilage defect.

Disclosed herein is a method of treating or repairing a cartilage defect, the method comprising implanting at the site of cartilage defect a bioactive implant.

Disclosed herein is a method of treating or repairing a cartilage defect, the method comprising implanting at the site of a cartilage defect a bioactive implant made by a method disclosed herein.

Disclosed herein is a method of treating or repairing a cartilage defect, the method comprising: preparing a composition comprising cartilage microparticles in a solution, wherein the size of the cartilage microparticles is from about 50 µm to about 900 µm; adding the composition to a mold; desiccating the composition, thereby producing the bioactive implant; and implanting the bioactive implant at the site of a cartilage defect.

Disclosed herein is a method of treating or repairing a cartilage defect, the method comprising: preparing a composition comprising cartilage microparticles in a hydroxyethyl starch solution, wherein the size of the cartilage microparticles is from about 50 µm to about 900 µm; adding the composition to a mold; desiccating the composition, thereby producing the bioactive implant; and implanting the bioactive implant at the site of a cartilage defect.

In an aspect, desiccating comprises producing a hardened bioactive implant having a predetermined size and shape.

In an aspect, the bioactive implant can be to treat or repair a traumatic loss or a degenerative loss of cartilage, or both, to treat or repair a cartilage defect following a tumor resection, to treat or repair a degenerative chondrol lesion, a traumatic chondral lesion, or both, or a combination thereof. In an aspect, the bioactive implant can be used to treat or repair one or more of these defects or conditions.

In an aspect, making the bioactive implant can comprise adding to a mold a composition comprising cartilage microparticles in a solution, wherein the size of the cartilage microparticles is from about 50 µm to about 900 µm, and desiccating the composition.

In an aspect, making the bioactive implant can comprise adding to a mold a composition comprising cartilage microparticles in a solution, and desiccating the composition.

In an aspect, a mold can have a predetermined size and a predetermined shape. In an aspect, a mold can have a volume from about 1 mL to about 120 mL. In an aspect, a mold can have a volume from about 500 mL to about 2000 mL. In an aspect, a mold can have a volume greater than 2000 mL. In an aspect, a mold can be customized for a specific cartilage defect or cartilage defects of the subject.

In an aspect, the size of the cartilage microparticles can range from about 50 µm to about 100 µm, from about 100 µm to about 150 µm, from about 150 µm to about 200 µm, from about 200 µm to about 250 µm, from about 250 µm to about 300 µm, from about 300 µm to about 350 µm, from about 350 µm to about 400 µm, from about 400 µm to about 450 µm, from about 450 µm to about 500 µm, from about 500 µm to about 550 µm, from about 550 µm to about 600 µm, from about 600 µm to about 650 µm, from about 650 µm to about 700 µm, from about 700 µm to about 750 µm, from about 750 µm to about 800 µm, from about 800 µm to about 850 µm, or from about 850 µm to about 900 µm.

In an aspect, making the bioactive implant can comprise preparing a disclosed composition. In an aspect, preparing a disclosed composition can comprise adding cartilage microparticles to a solvent to generate a solution. In an aspect, the solvent can comprise water. In an aspect, the solvent can comprise saline. In an aspect, the solvent can comprise DMSO. In an aspect, the solvent can comprise alcohol. In an aspect, the solvent can comprise a balanced salt solution. In an aspect, a balanced salt solution includes, but is not limited to, Hank's Balanced Salt Solution (HBSS), Earle's Balanced Salt Solution (EBSS), Phosphate-Buffered Saline (PBS), Dulbecco's Phosphate-Buffered Saline (DPBS), and combinations thereof.

In an aspect, the solution of a disclosed composition can comprise hydroxyethyl starch. In an aspect, the solution of a disclosed composition can comprise non-solubilized hydroxyethyl starch. In an aspect, the solution of a disclosed composition can comprise about 6% hydroxyethyl starch. In an aspect, a HES solution can be converted into a putty, a gel, or a paste. In an aspect, the HES solution can be converted into a putty, a gel, or a paste via evaporation or the introduction of cartilage microparticles. In an aspect, the HES solution can be converted into a putty, a gel, or a paste via evaporation or the introduction of additional cartilage chips, shavings, or powder. In an aspect, a disclosed HES solution is non-toxic. In an aspect, a disclosed HES solution comprises non-toxic components. In an aspect, a disclosed HES solution is safe for administration to human beings or other mammals.

In an aspect, the solution of a disclosed composition can comprise polyvinyl pyrrolidone (PVP). In an aspect, the PVP can comprise various molecular weights. In an aspect, the PVP can have an average molecular weight of 40,000. PVPs are known to the skilled person in the art. In an aspect, a PVP solution can be converted into a putty, a gel, or a paste. In an aspect, the PVP solution can be converted into a putty, a gel, or a paste via evaporation or the introduction of additional cartilage microparticles. In an aspect, the PVP solution can be converted into a putty, a gel, or a paste via evaporation or the introduction of additional cartilage chips, shavings, or powder. In an aspect, a disclosed PVP solution is non-toxic. In an aspect, a disclosed PVP solution comprises non-toxic components. In an aspect, a disclosed PVP solution is safe for administration to human beings or other mammals.

In an aspect, the solution of a disclosed composition can comprise povidone iodine. In an aspect, a povidone iodine solution can be converted into a putty, a gel, or a paste. In an aspect, the povidone iodine solution can be converted into a putty, a gel, or a paste via evaporation or the introduction of additional cartilage microparticles. In an aspect, the povidone iodine solution can be converted into a putty, a gel, or a paste via evaporation or the introduction of additional cartilage chips, shavings, or powder. In an aspect, a disclosed povidone iodine solution is non-toxic. In an aspect, a disclosed povidone iodine solution comprises non-toxic components. In an aspect, a disclosed povidone iodine solution is safe for administration to human beings or other mammals.

In an aspect, the solution of a disclosed composition can comprise collagen. In an aspect, collagen can be tendon collagen, bone collagen, or a combination thereof. In an aspect, a collagen solution can be converted into a putty, a gel, or a paste. In an aspect, the collagen solution can be converted into a putty, a gel, or a paste via evaporation or the introduction of additional cartilage microparticles. In an aspect, the collagen solution can be converted into a putty, a gel, or a paste via evaporation or the introduction of additional cartilage chips, shavings, or powder. In an aspect, a disclosed collagen solution is non-toxic. In an aspect, a disclosed collagen solution comprises non-toxic components. In an aspect, a disclosed collagen solution is safe for administration to human beings or other mammals.

In an aspect, the solution of a disclosed composition can comprise albumin. In an aspect, albumin can be human albumin, recombinant albumin, bovine albumin, non-bovine albumin, egg albumin, transgenic albumin, or a combination thereof. In an aspect, an albumin solution can be converted into a putty, a gel, or a paste. In an aspect, the albumin solution can be converted into a putty, a gel, or a paste via evaporation or the introduction of additional cartilage microparticles. In an aspect, the albumin solution can be converted into a putty, a gel, or a paste via evaporation or the introduction of additional cartilage chips, shavings, or powder. In an aspect, a disclosed albumin solution is non-toxic. In an aspect, a disclosed albumin solution comprises non-toxic components. In an aspect, a disclosed albumin solution is safe for administration to human beings or other mammals.

In an aspect, a disclosed solution can comprise one or more of the following solutes: hydroxyethyl starch (HES), non-solubilized HES, polyvinyl pyrrolidone (PVP), povidone iodine, bone collagen, tendon collagen, and albumin (e.g., human albumin, recombinant albumin, bovine albumin, non-bovine albumin, egg albumin, transgenic albumin). In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, a disclosed solution can comprise one or more of the following solutes: hydroxyethyl starch (HES), non-solubilized HES, polyvinyl pyrrolidone (PVP), povidone iodine, bone collagen, and tendon collagen, but not albumin. In an aspect, the amount of the one or more solutes can be from about 10% to about 90% w/v of the solution. In an aspect, the amount of the one or more solutes can be from about 10% to about 20% w/v of the solution. In an aspect, the amount of the one or more solutes can be from about 20% to about 30% w/v of the solution. In an aspect, the amount of the one or more solutes can be from about 30% to about 40% w/v of the solution. In an aspect, the amount of the one or more solutes can be from about 40% to about 50% w/v of the solution. In an aspect, the amount of the one or more solutes can be from about 50% to about 60% w/v of the solution. In an aspect, the amount of the one or more solutes can be from about 60% to about 70% w/v of the solution. In an aspect, the amount of the one or more solutes can be from about 70% to about 80% w/v of the solution. In an aspect, the amount of the one or more solutes can be from about 80% to about 90% w/v of the solution.

In an aspect, preparing a disclosed composition can comprise adding to the solution one or more agents. In an aspect, the agents can comprise therapeutic agents, bone morphogenetic proteins, anti-infective agents (e.g., anti-microbial agents, anti-fungal agents, and combinations thereof), growth factors, growth hormones, antibiotics, anti-oxidants, analgesics, vitamins (e.g., vitamin D, vitamin K, and combinations thereof), sterilizing agents (e.g., iodine, bromine, calcium salts, and combinations thereof).

In an aspect, the disclosed composition can comprise about 10% to about 70% w/v of cartilage microparticles, or about 10% to about 35% w/v of cartilage microparticles, or about 25% w/v of cartilage microparticles, or about 50% w/v of cartilage microparticles.

In an aspect, making the bioactive implant can comprise adding to a mold a composition comprising cartilage microparticles in a hydroxyethyl starch solution, wherein the size of the cartilage microparticles is from about 50 µm to about 900 µm, and desiccating the composition.

In an aspect, making the bioactive implant can comprise adding to a mold a composition comprising cartilage microparticles in a polyvinyl pyrrolidone (PVP) solution, wherein the size of the cartilage microparticles is from about 50 µm to about 900 µm, and desiccating the composition.

In an aspect, making the bioactive implant can comprise adding to a mold a composition comprising cartilage microparticles in a povidone iodine solution, wherein the size of the cartilage microparticles is from about 50 µm to about 900 µm, and desiccating the composition.

In an aspect, making the bioactive implant can comprise adding to a mold a composition comprising cartilage microparticles in a collagen solution, wherein the size of the cartilage microparticles is from about 50 µm to about 900 µm, and desiccating the composition.

In an aspect, making the bioactive implant can comprise adding to a mold a composition comprising cartilage microparticles in an albumin solution, wherein the size of the cartilage microparticles is from about 50 µm to about 900 µm, and desiccating the composition.

In a disclosed method of treating or repairing a cartilage defect, the implanted bioactive implant can be replaced by the subject's cartilage.

In an aspect of a disclosed method, one or more bioactive implants can be implanted.

In an aspect of a disclosed method, a subject can receive one or more bioactive implants.

In an aspect, a disclosed method of treating or repairing a cartilage defect can comprise evaluating the effect of the implanted bioactive implant at one or more pre-determined times. In an aspect, the pre-determined times can comprise 1 to 7 days day post-implantation, or a time between 1 and 7 days post-implantation. In an aspect, the pre-determined times can comprise 1 to 4 weeks post-implantation, or a time between 1 and 4 weeks post-implantation. In an aspect, the pre-determined times can comprise 1 to 12 months post-implantation, or a time between 1 and 12 months post-implantation. In an aspect, the pre-determined times comprise 1 to 10 years post-implantation, or a time between 1 and 10 years post-implantation.

In an aspect, evaluating the effect of the implanted bio-active implant can comprise examining the incorporation of the bioactive implant. In an aspect, examining the incorporation of the bioactive implant can use one or more radiograph. Using one or more radiographs, the skilled person (e.g., a radiologist, an orthopedic surgeon, etc.) can determine whether the bioactive implant has been successfully implanted.

In an aspect, a disclosed method of treating or repairing a cartilage defect can comprise evaluating the effect of the bioactive implant at one or more times post-implantation.

In an aspect, a disclosed method of treating or repairing a cartilage defect can comprise comprises systemically administering to the subject one or more agents. In an aspect, the one or more of agents can comprise therapeutic agents, bone morphogenetic proteins, anti-infective agents, growth factors, growth hormone, antibiotics, antioxidants, painkillers, vitamins, sterilizing agents, or a combination thereof. In an aspect, the one or more agents can be administered pre-implantation, during implantation, post-implantation, or a combination thereof. In an aspect, the one or more agents can be administered at one or more times. In an aspect, the one or more agents can be administered intravenously or orally.

In an aspect, one or more steps of a disclosed method can be modified, changed, repeated, or altered.

In an aspect, the cartilage microparticles can be embedded evenly or embedded unevenly in the desiccated composition. In an aspect, the desiccated composition can comprise both evenly and unevenly embedded cartilage microparticles.

In an aspect, a disclosed solution can comprise bone microparticles, wherein the size of the bone microparticles is from about 20 µm to about 800 µm.

The invention claimed is:

1. A method of preparing a bioactive implant, the method comprising:
    adding hydroxyethyl starch (HES), polyvinyl pyrrolidone (PVP), povidone iodine, collagen, and albumin to a solvent to form a HES-PVP-povidone iodine-collagen-albumin solution;
    adding cartilage microparticles to the HES-PVP-povidone iodine-collagen-albumin solution to form a composition comprising cartilage microparticles in the HES-PVP-povidone iodine-collagen-albumin solution, wherein the size of the cartilage microparticles is from about 50 µm to about 900 µm; and
    desiccating the composition comprising the cartilage microparticles in the HES-PVP-povidone iodine-collagen-albumin solution to produce a hardened bioactive implant.

2. The method of claim 1, wherein the hardened bioactive implant has a predetermined size and shape.

3. The method of claim 1, wherein the composition comprises about 25% w/v of cartilage microparticles.

4. The method of claim 1, wherein desiccating the composition comprises freeze-drying the composition.

5. The method of claim 1, wherein desiccating the composition comprises subjecting the composition to hypothermic dehydration.

6. The method of claim 1, wherein the solvent comprises water, saline, alcohol, or Dimethyl sulfoxide (DMSO).

7. The method of claim 1, wherein adding the HES, PVP, povidone iodine, collagen, and albumin to the solvent comprises dissolving the HES, PVP, povidone iodine, collagen, and albumin in the solvent to form a homogenous HES-PVP-povidone iodine-collagen-albumin solution in a single phase.

* * * * *